United States Patent
Glenn et al.

(10) Patent No.: US 7,887,589 B2
(45) Date of Patent: Feb. 15, 2011

(54) MINIMALLY INVASIVE SPINAL DISC STABILIZER AND INSERTION TOOL

(76) Inventors: Bradley J. Glenn, 1136 Pleasant Valley Dr., Oneida, WI (US) 54155; Gary A. Schneiderman, 2801 K St., Suite 410, Sacramento, CA (US) 95864

( * ) Notice: Subject to any disclaimer, the term of this patent is extended or adjusted under 35 U.S.C. 154(b) by 229 days.

(21) Appl. No.: 11/194,050

(22) Filed: Jul. 29, 2005

(65) Prior Publication Data

US 2007/0299521 A1    Dec. 27, 2007

Related U.S. Application Data

(60) Provisional application No. 60/665,874, filed on Mar. 29, 2005, provisional application No. 60/629,892, filed on Nov. 23, 2004.

(51) Int. Cl.
*A61F 2/44*    (2006.01)
(52) U.S. Cl. .................................. 623/17.14; 623/17.15
(58) Field of Classification Search .... 623/17.11–17.16
See application file for complete search history.

(56) References Cited

U.S. PATENT DOCUMENTS

| | | | |
|---|---|---|---|
| 4,759,766 A | | 7/1988 | Buettner-Janz et al. |
| 4,959,058 A | | 9/1990 | Michelson |
| D312,309 S | | 11/1990 | Michelson |
| 4,973,321 A | | 11/1990 | Michelson |
| D324,424 S | | 3/1992 | Michelson |
| 5,171,278 A | * | 12/1992 | Pisharodi .................... 128/898 |
| 5,258,031 A | * | 11/1993 | Salib et al. ............... 623/17.15 |
| 5,314,477 A | | 5/1994 | Marnay |
| 5,401,269 A | | 3/1995 | Buttner-Janz et al. |
| 5,425,773 A | * | 6/1995 | Boyd et al. .............. 623/17.15 |
| 5,451,227 A | | 9/1995 | Michaelson |
| 5,505,732 A | | 4/1996 | Michelson |
| 5,534,029 A | * | 7/1996 | Shima ..................... 623/17.15 |
| 5,674,294 A | * | 10/1997 | Bainville et al. ......... 623/17.16 |
| 5,741,253 A | | 4/1998 | Michelson |

(Continued)

FOREIGN PATENT DOCUMENTS

WO    WO-01/64142    9/2001

(Continued)

OTHER PUBLICATIONS

"expand." Merriam-Webster Online Dictionary, [online], Retrieved from the Internet <URL: http://www.m-w.com/dictionary/expand>.*

(Continued)

*Primary Examiner*—Eduardo C Robert
*Assistant Examiner*—Ellen C. Hammond
(74) *Attorney, Agent, or Firm*—Heisler & Associates

(57) ABSTRACT

The invention relates to a spinal implant to be inserted between two vertebra to support and stabilize adjacent vertebra and allow for physiological motion. One embodiment of the implant includes an upper assembly and a lower assembly, where the assemblies are adapted to articulate relative to one another. This implant also includes elongate elements that are deployable between a closed position and an open position. Portions of the implant can interlock to form various shapes. The invention includes an implantable device to support the vertebrae, and a minimally invasive method for inserting and deploying the device within the intervertebral space.

26 Claims, 30 Drawing Sheets

U.S. PATENT DOCUMENTS

| | | | |
|---|---|---|---|
| 5,772,661 A | | 6/1998 | Michelson |
| 5,860,977 A | * | 1/1999 | Zucherman et al. .......... 606/61 |
| 5,895,428 A | * | 4/1999 | Berry ..................... 623/17.15 |
| 6,179,874 B1 | | 1/2001 | Cauthen |
| 6,224,595 B1 | | 5/2001 | Michelson |
| 6,368,351 B1 | * | 4/2002 | Glenn et al. ............. 623/17.15 |
| 6,387,130 B1 | * | 5/2002 | Stone et al. ............. 623/17.16 |
| 6,436,098 B1 | | 8/2002 | Michelson |
| 6,440,168 B1 | | 8/2002 | Cauthen |
| 6,485,517 B1 | | 11/2002 | Michelson |
| 6,572,653 B1 | | 6/2003 | Simonson |
| 6,575,977 B1 | | 6/2003 | Michelson |
| 6,679,915 B1 | | 1/2004 | Cauthen |
| 6,692,495 B1 | | 2/2004 | Zacouto |
| 6,695,849 B2 | | 2/2004 | Michelson |
| 6,733,535 B2 | | 5/2004 | Michelson |
| 6,770,074 B2 | | 8/2004 | Michelson |
| 6,808,537 B2 | | 10/2004 | Michelson |
| 6,852,126 B2 | * | 2/2005 | Ahlgren .................. 623/17.11 |
| 6,869,446 B2 | | 3/2005 | Ralph et al. |
| 6,896,676 B2 | | 5/2005 | Zubok et al. |
| 6,896,680 B2 | | 5/2005 | Michelson |
| 6,949,123 B2 | * | 9/2005 | Reiley .................... 623/17.11 |
| 7,270,682 B2 | * | 9/2007 | Frigg et al. ............. 623/17.16 |
| 2002/0082693 A1 | * | 6/2002 | Ahlgren .................. 623/17.11 |
| 2002/0151976 A1 | | 10/2002 | Foley et al. |
| 2004/0059421 A1 | * | 3/2004 | Glenn et al. ............. 623/17.16 |
| 2004/0093082 A1 | * | 5/2004 | Ferree .................... 623/17.11 |
| 2004/0153159 A1 | | 8/2004 | Cauthen |
| 2004/0225361 A1 | | 11/2004 | Glenn et al. |
| 2005/0021144 A1 | | 1/2005 | Malberg et al. |
| 2005/0043800 A1 | * | 2/2005 | Paul et al. ............... 623/17.15 |
| 2005/0261768 A1 | * | 11/2005 | Trieu ..................... 623/17.11 |
| 2007/0073398 A1 | | 3/2007 | Fabian et al. |
| 2008/0103597 A1 | * | 5/2008 | Lechmann et al. ....... 623/17.16 |

FOREIGN PATENT DOCUMENTS

| | | |
|---|---|---|
| WO | WO-02/05733 | 1/2002 |

OTHER PUBLICATIONS

International Search Report for PCT/US2005/042892 dated Aug. 18, 2006, 2 pp.

The World's First Artificial Disc, website: http://www.charitedisc.com/charitedev/domestic/patients/about_worldfirst.asp, accessed Mar. 14, 2005, 1 pp.

What is the CHARITE™ Artificial Disc?, website: http://www.charitedisc.com/charitedev/domestic/patients/about_whatisCHARITE.asp, accessed Mar. 14, 2005, 1 pp.

What are the Potential Benefits and Risks of Disc Replacement Surgery?, website: http://www.charitedisc.con/charitedev/domestic/patients/about_benefits.asp., accessed Mar. 14, 2005, 2 pp.

FDA Approves first Artificial Disc for treatment of low back pain new motion preserving device offers alternative to spinal fusion surgery, website: http://www.charitedisc.com/charitedev/domestic/patients/popup_October04.htm, accessed Mar. 14, 2005, 2 pp.

The CHARITE™ Artificial Disc, http://www.charitedisc.com/charitedev/domestic/physicians/about.asp, accessed Mar. 14, 2005, 1 pp.

Training, website: http://www.charitedisc.com/charitedev.domestic/physicians/training.asp, accessed Mar. 14, 2005, 1 pp.

Disc Replacement Surgery, website: http://www.spine-surgery.com/SSPSC/Artificial%20Disc%20Replacement/discreplacement, accessed Mar. 14, 2005, 5 pp.

Tetris, website: http://www.signusmedical.com/TetrisUS.aspx, accessed May 23, 2005, 2 pp.

* cited by examiner

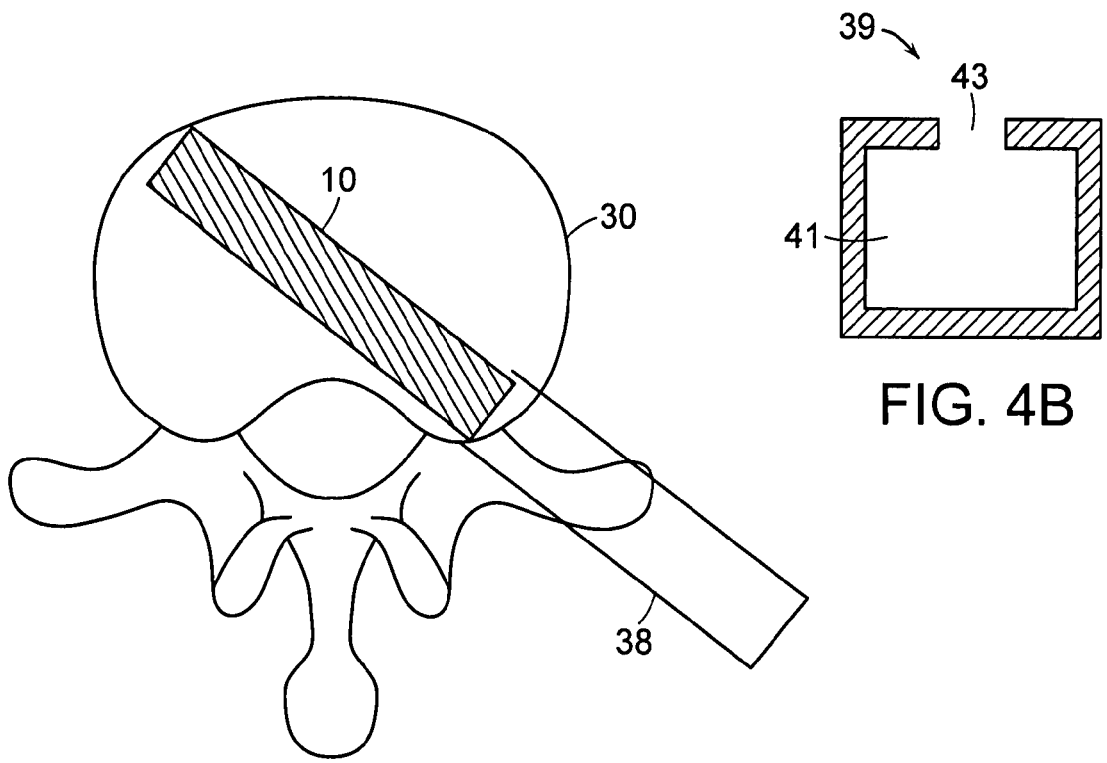
FIG. 4A
FIG. 4B
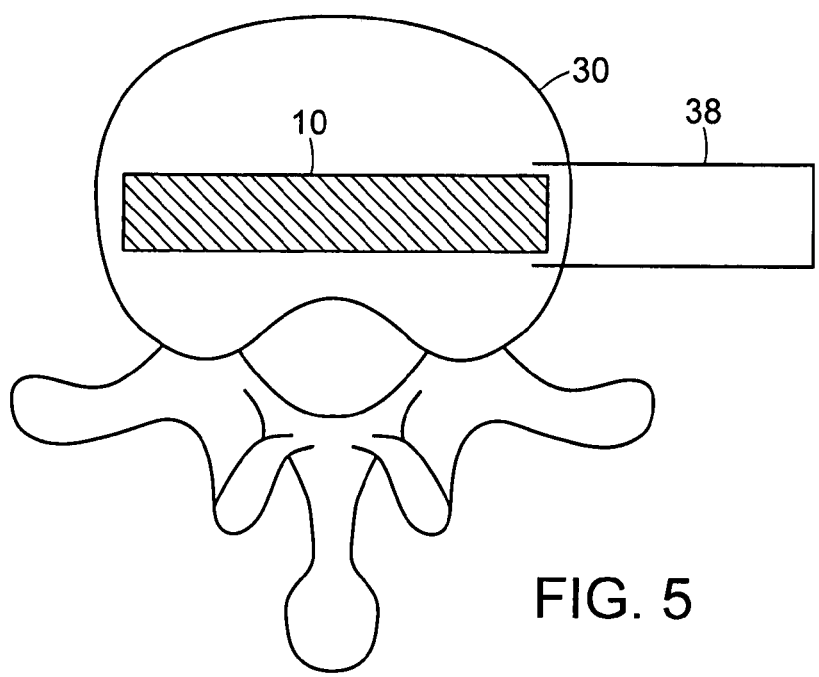
FIG. 5

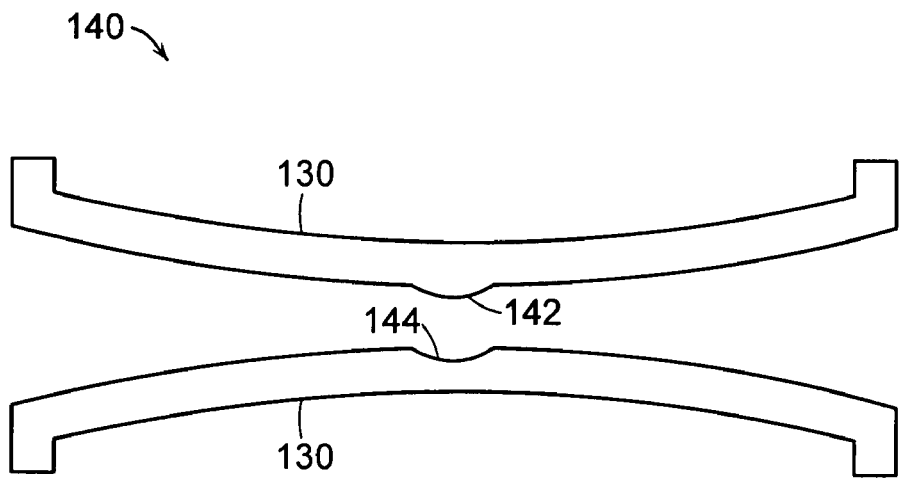
FIG. 16
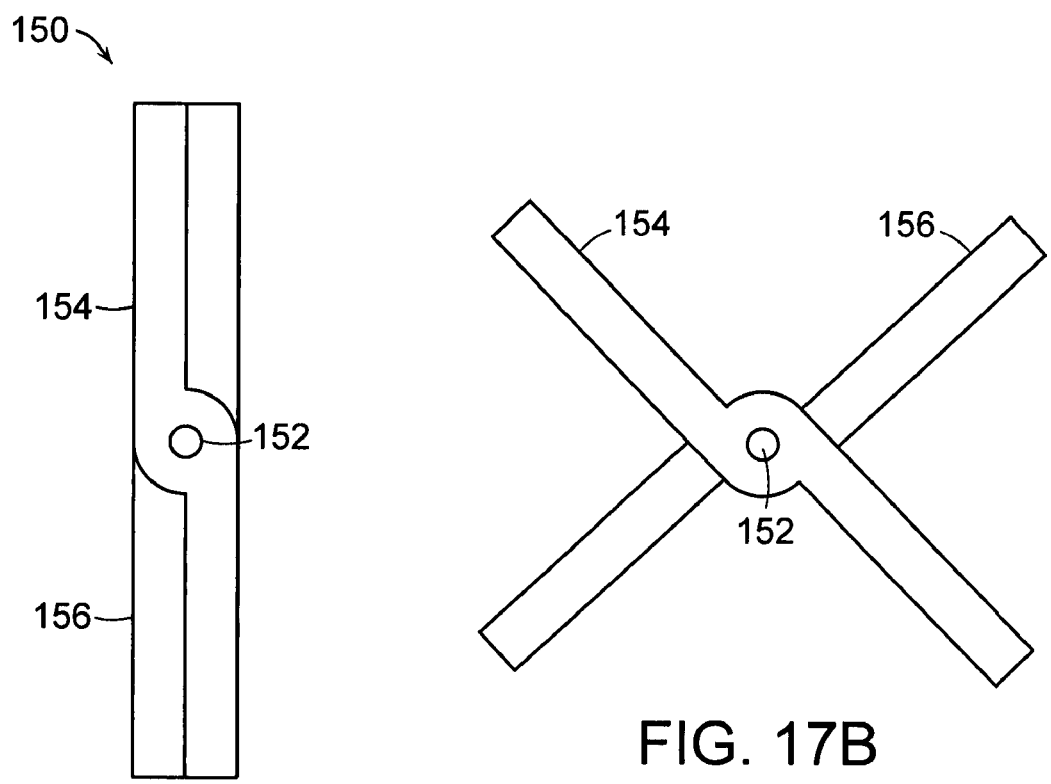
FIG. 17A
FIG. 17B

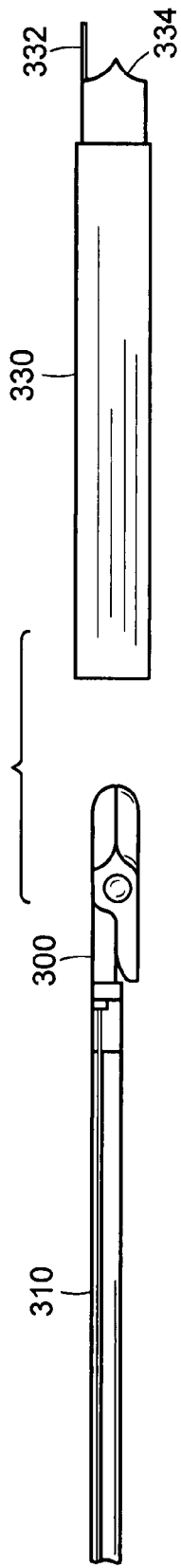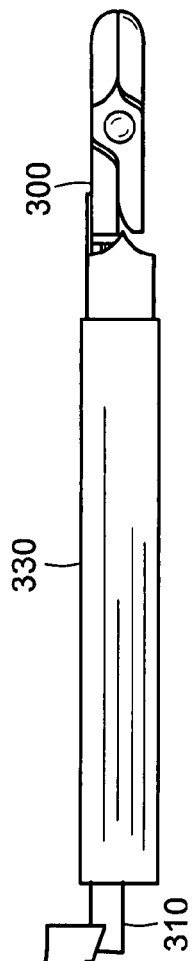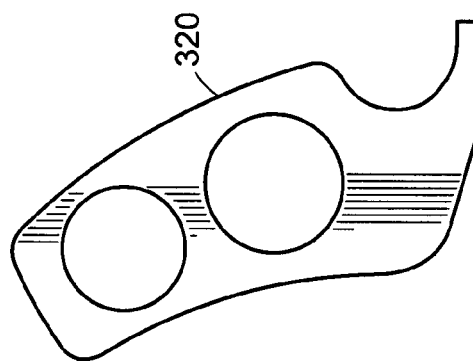
FIG. 39
FIG. 40

MINIMALLY INVASIVE SPINAL DISC STABILIZER AND INSERTION TOOL

CROSS-REFERENCE TO RELATED APPLICATIONS

This application claims priority to and the benefit of U.S. provisional patent application Ser. No. 60/629,892, filed Nov. 23, 2004, and U.S. provisional patent application Ser. No. 60/665,874, filed Mar. 29, 2005, the disclosures of which are being incorporated herein by reference in their entirety.

FIELD OF THE INVENTION

The present invention relates generally to the field of spinal implants and, more particularly, to an implant that is configured to be placed within an intervertebral space in order to support and stabilize adjacent vertebra and allow for physiological motion.

BACKGROUND OF THE INVENTION

The vertebrate spine is the axis of the skeleton on which a substantial portion of the weight of the body is supported. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints, but allow known degrees of flexion, extension, lateral bending, and axial rotation.

The typical vertebra has a thick anterior bone mass called the vertebral body, with a neural (vertebral) arch that arises from the posterior surface of the vertebral body. The spaces between adjacent vertebrae are supported by intervertebral discs. Each neural arch combines with the posterior surface of the vertebral body and encloses a vertebral foramen. The vertebral forming of adjacent vertebrae is aligned to form a vertebral canal, through which the spinal sac, cord, and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus"), and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The annulus of the disc is a tough, outer fibrous ring which binds together adjacent vertebrae. The fibrous portion, which is much like a laminated automobile tire, measures about 10 to 15 millimeters in height and about 15 to 20 millimeters in thickness. The fibers of the annulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Located within the annulus is the nucleus. The healthy nucleus is largely a gel-like substance having a high water content, and like air in a tire, serves to keep the annulus tight yet flexible. The nucleus-gel moves slightly within the annulus when force is exerted on the adjacent vertebrae while bending, lifting, and other motions.

The spinal disc may be displaced or damaged due to trauma, disease, degenerative defects, or wear over an extended period of time. A disc herniation occurs when the annulus fibers are weakened or torn and the inner tissue of the nucleus becomes permanently bulged, distended, or extruded out of its normal, internal annulus confines. The mass of a herniated or "slipped" nucleus tissue can compress a spinal nerve, resulting in leg pain, loss of muscle control, or even paralysis. Alternatively, with degeneration of a disc, the nucleus loses its water binding ability and deflates, as though the air had been let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Back pain related to the aforementioned damaged or displaced intervertebral disc is a very common health problem, affecting the majority of people at some point in their life. The current treatment for back pain without sciatica is conservative care. However, when this fails, fusion of the spinal segment is the most common practice. The intervertebral disc is removed, and the vertebrae are supported by the placement of various implants that help promote fusion of the adjacent vertebrae. While this treatment alleviates the pain, all discal motion is lost in the fused segment. Ultimately, this procedure places a greater stress on the discs adjacent to the fused segment as they compensate for lack of motion, perhaps leading to premature degeneration of those adjacent discs.

It is recognized by spine surgeons that it would be preferable to maintain physiological motion of the spinal segment. Accordingly, as an alternative to vertebral fusion, a number of implants which have been designed to act as an artificial disc which would preserve motion. The first implants, or prosthetic discs, embody a wide variety of ideas, such as ball bearings, springs, metal spikes and other perceived aids. These prosthetics are all made to replace the entire intervertebral disc space and are large and rigid. Beyond the questionable applicability of the devices is the inherent difficulties encountered during implantation. Due to their size and inflexibility, these devices require an anterior implantation approach as the barriers presented by the lamina and, more importantly, the spinal cord and nerve rootlets during posterior or posterior lateral implantation are difficult to avoid.

Anterior implantation, however, can involve numerous risks during surgery. Various organs present physical obstacles as the surgeon attempts to access the damaged disc area from the front of the patient. After an incision into the patient's abdomen, the surgeon is forced to navigate around interfering organs and carefully move them aside in order to gain access to the spine. One risk to the patient from an anterior approach is that these organs may be inadvertently damaged during the procedure. Currently, as a result of the limitations of the available implants, and the difficulty and complications related to surgically implanting the current devices, their use has been limited.

In contrast, a posterior approach to intervertebral disc implantation avoids the risks of damaging body organs.

Despite this advantage, a posterior approach also raises other difficulties that have discouraged it use. For instance, a posterior approach can introduce a risk of damaging the spinal cord. Additionally, vertebral body geometry allows only limited access to the intervertebral discs. Thus, the key to successful posterior or posterior lateral implantation is avoiding contact with the spinal cord and nerves, as well as being able to place an implant through a limited area due to the shape of the vertebral bones. Because an anterior approach does not present the space limitations that occur with a posterior approach, current prosthetic disc designs are too bulky to safely use with a posterior approach. Therefore, a substantial need exists for a low profile prosthetic spinal disc capable of being implanted into an intervertebral space, and a method of surgically implanting the low profile prosthetic spinal disc into the intervertebral disc space through a posterior approach with minimal contact with the spinal cord and nerves and minimum damage to the surrounding soft tissue.

SUMMARY OF THE INVENTION

There are two general approaches to an artificial disc: one is a complete replacement of the entire joint, where an articulated prosthesis is solidly attached to the adjacent vertebra. A second approach is to replace only the center "nucleus" of the disc with an implant which provides compliant support in the center of the disc space but retains the native support of the annulus fibrosis and supportive ligaments. The current invention adopts the advantages of both strategies, providing a minimally invasive support device in the center of the disc, while distributing the axial load to the robust peripheral cortical bone of the vertebrae. Also, the device maintains the majority of the annulus, as only a small portal is required for insertion. The device further allows for physiological motion between the vertebral bodies.

In one aspect, the invention relates to an intervertebral implant including an upper assembly having at least two elongate elements and a lower assembly having at least two elongate elements. Alternatively, either the upper assembly or the lower assembly may have only a single elongate element or plate. The upper assembly is adapted to articulate relative to the lower assembly.

In another aspect, the invention relates to an intervertebral implant including an upper assembly having at least one elongate element and a lower assembly having at least one elongate element interlocked with the upper assembly. The upper assembly can be adapted to enable a limited range of motion between the interlocked elements, for example rotational motion.

In various embodiments of the foregoing aspects, the at least two elongate elements of at least one of the upper assembly and the lower assembly interlock to form various shapes, such as, for example, A, H, I, K, M, N, T, V, W, X, Y, and Z. At least one of the elongate elements may include a bend. In one embodiment, the interlocked elongate elements may define a clearance therebetween to enable a limited range of motion between the elements in an interlocked arrangement. The at least two elongate elements of at least one of the upper assembly and the lower assembly can be deployed between a closed position and an open position. Deployment can be effected either manually or automatically by, for example, a shape memory material, springs, and/or other mechanical means. In one embodiment, the at least two elongate elements form an I shape, or other low-profile shape, in the closed position. In some embodiments, the at least two elongate elements form any of the aforementioned shapes when in the open position.

Additionally, the at least two elongate elements can be positioned through a predetermined angular range between the closed position and the open position. In various embodiments, the predetermined angular range comprises a value greater than about 0 degrees and less than about 180 degrees. The at least two elongate elements can be secured by, for example, a pivot or similar joint. In various embodiments, the implant further includes a locking mechanism for preventing relative movement between the elongate elements. The locking mechanism can be manually or automatically activated by, for example, a shape memory material, springs, screws, pins, linkages, and/or other mechanical means.

In various embodiments, the implant or components thereof may be manufactured from any biocompatible material, such as, for example, stainless steel, aluminum, tantalum, gold, titanium, ceramic, chromium, cobalt, nitinol, metal/ceramic matrices, polytetrafluoroethylene (PTFE), thermoplastic polyurethane (TPU); ethylene vinyl acetate (EVA); thermoplastic polyether block amides; thermoplastic polyester elastomers, nylons, silicones; polyethylenes; polyamides, polyetheretherketone (PEEK), and combination thereof.

Further, at least one of the upper assembly and the lower assembly can be adapted for engaging an adjacent vertebral surface. For example, the assemblies can include projections for engaging the bone or apertures for enabling in-growth of bone. Additionally, the implant can be coated or otherwise treated with, for example, a biological or therapeutic agent. In some embodiments, the implant includes an articulation region disposed on each of the upper assembly and the lower assembly. The articulation regions can include a protuberance disposed on one of the upper and lower assembly and a mating recess disposed on the other assembly, the protuberance and recess at least partially in contact. The articulation regions can be, for example, a ball and socket configuration, a male to female configuration, mating arcuate surfaces, or corresponding saddles. In one embodiment, at least one of the elongate elements tapers along a length thereof. The implant may include a spacer disposed between the upper assembly and the lower assembly. Additionally, the articulation region can be expandable to increase the overall bearing surface between the upper and lower assemblies.

In another aspect, the invention relates to an intervertebral implant including a first elongate element having a first surface and a second opposing surface and a second elongate element having a first surface and a second opposing surface. The first surfaces are substantially planar. The second surfaces include complimentary mating articulation regions for enabling relative movement of the first elongate element and the second elongate element. In one embodiment, the articulation regions are disposed proximate a midpoint on each second surface.

In various embodiments, the first elongate element is oriented substantially parallel to the second elongate element. The first surface of at least one of the first element and the second element is adapted for engaging an adjacent vertebral surface. The articulation regions of the implant may include a protuberance disposed on one of the elongate elements and a mating recess disposed on the other elongate element, the protuberance and recess at least partially in contact. The complimentary mating articulation regions can be, for example, a ball and socket configuration, a male to female configuration, mating arcuate surfaces, or corresponding saddles. The implant may include a spacer disposed between the second surfaces of the first elongate element and the second elongate element, the spacer replicating the articulation regions. The second surfaces of the first element and the second element may taper along a length thereof. The implant may include at least one aperture for enabling in-growth of bone.

Additionally, the implant may include a third elongate element including a first substantially planar surface and a second opposing surface defining a notch, wherein the notch engages the first surface of the first elongate element. In one embodiment, the notch bisects the third elongate element. The third element may be disposed above and substantially perpendicular to the first elongate element. Further, the implant may include a fourth elongate element including a substantially planar first surface and a second opposing surface defining a notch, wherein the notch of the fourth elongate element engages the second elongate element. In one embodiment, the notch defined by the fourth elongate element bisects the fourth elongate element. The fourth element may be disposed below and substantially perpendicular to the second elongate element. In one embodiment, the first elongate element and the second elongate element each define a notch disposed in the first surfaces thereof. The notch of the first element mating with the notch of the third element and the notch of the second element mating with the notch of the fourth elongate element. The first surfaces of at least one of the first and third elongate elements and the second and fourth elongate elements are substantially coplanar. The notches may include arcuate and/or tapered sidewalls for providing clearance between the elongate elements for relative rotational movement between the elongate elements.

In another aspect, the invention relates to an intervertebral implant including a first elongate element having a resilient body adapted for contacting a proximate vertebral surface at, at least two contact regions, and a second elongate element having a resilient body adapted for contacting a proximate vertebral surface at, at least two contact regions. The first and second elongate elements include articulation regions disposed along their respective resilient bodies between the contacting regions. The first elongate element and the second elongate element can be mated via the articulation regions.

In various embodiments of the foregoing aspect, at least one of the resilient bodies includes an arcuate shape. The first elongate element may be oriented substantially perpendicular to the second elongate element. In one embodiment, the articulation regions are disposed within notches formed in the first and second elongate elements.

In another aspect, the invention relates to an intervertebral implant including a first elongate element and a second elongate element. The first elongate element includes a first base plate for engaging an adjacent vertebral surface and a first resilient plate coupled to the first base plate. The second elongate element includes a second base plate for engaging an adjacent vertebral surface and a second resilient plate coupled to the second base plate. The first resilient plate and the second resilient plate are adapted to mate together to allow relative movement between the first elongate element and the second elongate element.

In one embodiment, the resilient plates are non-planar. The plates may each have an elongate shape. The first resilient plate is coupled to the first base plate at the ends thereof, and the second resilient plate is coupled to the second base plate at the ends thereof. The first and second resilient plates may define slots in the outside surfaces thereof for inter-engagement.

In another aspect, the invention relates to an intervertebral implant including a first element and a second element. The first element includes a proximal portion and a distal portion, each extending from a central portion of the first element. The proximal portion and the distal portion extend in opposite directions and are offset relative to a longitudinal axis of the first element. The second element includes a proximal portion and a distal portion, each extending from a central portion of the second element. The proximal portion and the distal portion extend in opposite directions and are offset relative to a longitudinal axis of the second element. The first element includes a first articulation region disposed on a first surface of the central portion of the first element, and the second element includes a second articulation region disposed on a first surface of the central portion of the second element adapted for mating with the first articulation region. The first and second articulation regions are at least partially in contact for enabling relative movement between the first element and the second element.

In various embodiments, the longitudinal axes bisect the central portions of the first and second elements and the corresponding proximal and distal portions are evenly spaced about their respective longitudinal axis. The implant may further include a third element including a proximal portion and a distal portion, each extending from a central portion of the third element. The proximal portion and the distal portion extend in opposite directions and are offset relative to a longitudinal axis of the third element. The proximal and distal portions of the third element are oriented complimentarily to the proximal and distal portions of the first element. The third element mating with a second opposing surface of the first element. The central portions of the first element and the third element have reduced thicknesses relative to the proximal and distal portions of the first and third elements, such that a first surface of the third element is substantially coplanar with the second surface of the first element when mated.

Additionally, the implant may further include a fourth element including a proximal portion and a distal portion, each extending from a central portion of the fourth element. The proximal portion and the distal portion extend in opposite directions and are offset relative to a longitudinal axis of the fourth element. The proximal and distal portions of the fourth element are oriented complimentarily to the proximal and distal portions of the second element. The fourth element mating with a second opposing surface of the second element. The central portions of the second element and the fourth element have reduced thicknesses relative to the proximal and distal portions of the second and fourth elements, such that a first surface of the fourth element is substantially coplanar with the second surface of the second element when mated.

Further, the third element may be secured to the first element and the fourth element may be secured to the second element by pivot joints. At least a portion of the first surfaces of the third and fourth elements can be adapted to mate with a vertebral surface. The implant may include a locking mechanism for preventing relative movement between the first element and the second element. The first element and the second element are capable of relative rotational movement and the locking mechanism is capable of locking the first element at an angle of rotation relative to the second element. The angle of rotation may be from about 0 degrees to about 90 degrees.

In another aspect, the invention relates to a tool for deploying an intervertebral implant. The tool includes a first body adapted to be coupled to a first portion of the implant and a second body adapted to be coupled to a second portion of the implant. The second body is slidably coupled to the first body. The first body and second body may be slidably coupled via a tongue and groove joint. The second body may include a wedge shaped proximal end. The tool may include a handle extending from the first body.

In various embodiments, a distal end of the second body is coupled to the implant when positioning the implant. The second body adapted to be decoupled from the first body to orient the proximal end in contact with the implant for deploying the implant. Deploying the implant may include moving the wedge shaped proximal end between the first portion and the second portion of the implant to move the second portion away from the first portion of the implant. The first portion of the implant and the second portion of the implant may be pivotably coupled to enable relative rotational movement of the second portion relative to the first portion of the implant.

In another aspect, the invention relates to a tool for deploying an intervertebral implant. The tool includes an elongate body adapted to be coupled to a portion of the implant and a handle extending therefrom. The elongate body has a wedge shaped projection extending from a distal portion of the elongate body. The distal portion of the tool can mate with the implant. The tool displaces a first portion of the implant relative to a second portion of the implant upon rotation of the tool.

In another aspect, the invention relates to a method for installing an intervertebral implant, The method includes the steps of providing the intervertebral implant, coupling the intervertebral implant to a tool, and implanting the implant into a body relative to two adjacent vertebrae. The implant has two portions capable of relative movement, and the tool has a first body adapted to be coupled to a first portion of the implant and a second body adapted to be coupled to a second portion of the implant. The second body is slidably coupled to the first body and has a wedge shaped proximal end. The method further includes the steps of decoupling the second body from the tool; reorienting and recoupling the second body to the tool, such that the wedge shaped proximal end contacts at least a portion of the implant; and moving the second body towards the implant to separate the first portion from the second portion. Alternatively, the method could be carried out with use of a cannula, wherein an implant is coupled to a tool and both implant and tool are passed though the cannula, inserted within the body to facilitate insertion of the implant into the intervertebral space. An elongated tool with a wedge, or other appropriately shaped tool, can be passed along the cannula to separate the first portion of the implant from the second portion of the implant.

In various embodiments, the method further includes the step of decoupling the tool from the implant. In one embodiment, the implanting step is performed at least one of laterally, posterior-laterally, and anterior-laterally. The first portion of the implant may be pivotably coupled to the second portion of the implant for enabling relative rotational movement. The method may further include the step of locking the first portion of the implant at an angle relative to the second portion of the implant.

In another aspect, the invention relates to an intervertebral implant including an upper assembly defining a first vertebral contact surface and a lower assembly defining a second vertebral contact surface and adapted to articulate relative to the upper assembly. At least one of the first vertebral contact surface and the second vertebral contact surface comprises an expandable surface area.

In another aspect, the invention relates to an intervertebral implant including an upper assembly and a lower assembly supporting the upper assembly and adapted to articulate relative to the upper assembly. At least one of the upper assembly and the lower assembly is configured to include an expandable vertebral contact surface area.

In another aspect, the invention relates to an intervertebral implant including an upper assembly having at least two elements, the at least two elements configurable to vary a size of a vertebral contact surface area of the upper assembly, and a lower assembly supporting the upper assembly, the lower assembly comprising at least two elements, the at least two elements configurable to vary a size of a vertebral contact surface of the lower assembly.

In another aspect, the invention relates to an intervertebral implant including an upper assembly and a lower assembly coupled to the upper assembly through mating articulation regions. The articulation regions comprise expandable bearing surfaces.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 4A is a schematic top view of the intervertebral implant of FIG. 1 being inserted into a intervertebral space through a posterior-lateral approach, in accordance with one embodiment of the invention;

FIG. 4B is a schematic end view of the insertion tool depicted in FIG. 4A, in accordance with one embodiment of the invention;

FIG. 5 is a schematic top view of the intervertebral implant of FIG. 1 being inserted into a intervertebral space through a lateral approach, in accordance with one embodiment of the invention;

FIG. 16 is a schematic side view of an intervertebral implant comprising two parallel arched elements, in accordance with one embodiment of the invention;

FIG. 17A is a schematic top view of a two component "scissors" type element of an intervertebral implant in a closed configuration, in accordance with one embodiment of the invention;

FIG. 17B is a schematic top view of the "scissors" type element of FIG. 17A in an open configuration;

FIG. 39 is a schematic top view of the intervertebral implant and insertion tool of FIG. 37 being inserted through an insertion housing;

FIG. 40 is a schematic top view of the intervertebral implant and insertion tool inserted in the insertion housing of FIG. 39;

DETAILED DESCRIPTION

The invention provides an apparatus for implantation between two vertebrae of a spinal column to replace or alleviate stress upon an intervertebral disc. The apparatus comprises at least one upper assembly and one lower assembly that can articulate about a mechanical connection between the upper and lower assemblies, thus allowing for controlled relative motion of the at least two assemblies. As a result, when placed between and attached to or resting against two vertebrae, the implant permits controlled motion between vertebral segments of the axial skeleton, similar to that provided by the intervertebral disc being replaced or supported.

The invention also provides a method and apparatus for implanting the apparatus within the intervertebral space. The method employs a minimally invasive or open lateral, anterior-lateral, or posterior-lateral approach that minimizes soft tissue damage around the implant. The apparatus for inserting the implant may be used both to insert the implant and deploy the implant into a working configuration within the intervertebral space.

Figure 1:
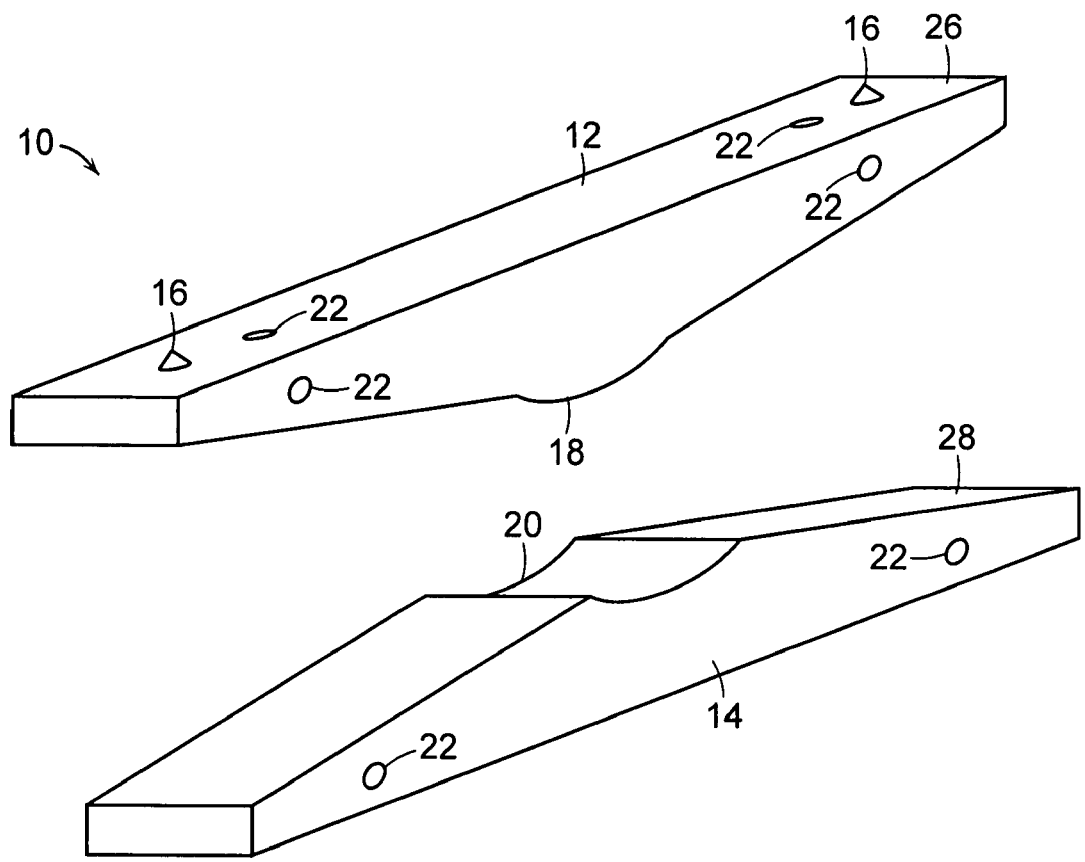
FIG. 1 is a schematic perspective view of an intervertebral implant with two parallel elongate elements, in accordance with one embodiment of the invention.

FIG. 1 is a schematic perspective view of an intervertebral implant with two separate parallel elongate elements. The implant 10 includes an upper elongate element 12 and a lower elongate element 14 that contact each other through a mating articulation region located generally about a central region of each element. In this configuration, the mating articulation region includes complementary portions on the upper elongate element 12 and the lower elongate element 14, such that the convex or male mating articulation region 18 on the upper elongate element 12 mates with a concave or female mating articulation region 20 on the lower elongate element 14.

The upper elongate element 12 and the lower elongate element 14 both have a substantially rectangular profile with substantially straight 90 degree edges. In alternative embodiments, the elongate elements may form oblong, elliptical, or other appropriately shaped profiles, while the edges of the elongate elements may be rounded, curved, chamfered, or otherwise shaped to allow for easier insertion into, and better and safer use within, the intervertebral space.

The mating articulation regions are designed to allow relative motion between the upper elongate element 12 and lower elongate element 14 such that the elements can articulate, pivot, pitch, or rotate about the center of the mating articulation portion without any misalignment of the two elements. This articulation between the upper and lower elements of the implant device can allow for physiological motion of the spine, such as flexion, extension, lateral bending, and/or physiological translation.

In some embodiments, the upper and lower portions of the mating articulation can fit together with a loose connection, allowing a certain amount of play between the two articulation portions. As a result, the upper elongate element 12 and lower elongate element 14 may be free to articulate or pivot about the center of the mating articulation. In certain alternative configurations, the upper and lower portions of the mating articulation can fit together snuggly, either connecting the two elements of the implant 10 together in a rigid position, or limiting the articulation available between the two elements to a predetermined amount. The mating articulation can include, but is not limited to, a ball and socket type connection, a protuberance and saddle, or other appropriate complementary articulation connection. Selection of an appropriate mating articulation can allow the elements to pivot with respect to each other in only one direction, for example along the lengthwise axis of the elongate elements, or pivot in any direction around the central axis of the mating articulation.

Both the upper elongate element 12 and the lower elongate element 14 include a vertebral surface 26, defining the outer portion of the implant 10, that contacts the upper and lower vertebrae respectively, and an articular surface 28 in the inner portion of the implant 10. The vertebral surface 26 of each element is substantially flat, while the articular surface 28 of each element is beveled such that each element is thinner at its ends and thicker towards its central region. This beveling or tapering of the articular surfaces 28 of each element allows for a greater range of motion as the upper elongate element 12 and the lower elongate element 14 articulate or pivot with respect to each other about the mating articulation. Changing the angle of the bevel on each articular surface 28 can therefore change the range of motion available to the implant 10.

In alternative embodiments of the invention, the articular surfaces 28 can be of a different shape, such as, but not limited to, a flat or curved surface, depending upon the required articulation of the implant 10. In certain embodiments, the shape of the articular surface 28 of the upper elongate element 12 and the lower elongate element 14 can differ, while in further embodiments, the shape of the articular surface 28 on either side of a single element may also differ. In some embodiments of the invention, the vertebral surfaces 26 of one or both elements of the implant 10 can also include a beveled and/or curved portion, depending upon the specific requirements of the implant.

Projections 16 can be attached or otherwise formed on the vertebral surfaces 26 of one or both elements of the implant 10, allowing the vertebral surfaces 26 to better contact or affix to the vertebrae directly above and below the implant 10. The projections 16 may have various forms to interact securely with the vertebra. These forms may include, but are not limited to, a single or a plurality of spikes, hooks, or other raised elements for imbedding securely into the vertebra. In alternative embodiments, the projections 16 can include knurled, grooved, ribbed, or otherwise textured regions of the vertebral surface to provide a more secure contact with the vertebra above and below the implant 10. In further alternative embodiments, the projections 16 can be replaced by, or assisted by, an adhesive substance such as, but not limited to, a biological adhesive, that can be placed on a region of the vertebral surface 26, and/or one or more side, of one or more elongate elements to improve the contact between vertebra and implant 10.

The upper and lower elements of the implant can include, either in conjunction with or in place of the projections 16 and/or adhesive described above, a single or a plurality of indentations 22, such as, but not limited to, holes, gaps or other surface properties, along the vertebral surface 26 and sides of each element of the implant 10. These indentations can promote bone growth into the implant to fuse the implant to the vertebra.

In alternative embodiments of the invention, the projections 16, adhesive, and/or indentations 22 can be placed only on one of the upper 12 and lower 14 elements of the implant 10. In certain embodiments, indentations 22 may be placed only on certain surfaces of each element, such as, for example, only on the vertebral surfaces 26 of each elongate element. It should be noted that any combination of the above methods of improving contact between the implant 10 and the vertebrae may be placed on any of the outer surfaces (i.e., the vertebral surfaces 26 and the sides and ends of each element 12,14), and it is not necessary to have the same combination of elements on any two sides. As such, different configurations of contact improving methods may be employed on different surfaces, depending on the particular requirements of the implant 10 and the particular geometry and physiology of the spine of a patient. In a further alternative embodiment, one or both of the elongate elements may be free from any projections 16, indentations 22, and/or adhesive, with pressure from the vertebrae above and below the implant 10 holding the implant 10 in place. In a further alternative embodiment, separate locking elements can be deployed within the intervertebral space to secure the implant 10 to the vertebrae.

Furthermore, the implant 10 can be coated or otherwise treated with biological or therapeutic agents to, for example, promote bone growth or treat infection. In further alternative embodiments, the implant may include a mechanism, such as, but not limited to, a cannula and micro-pump, to allow for the delivery of a biological or therapeutic agent to the spinal column from an internal or external storage reservoir.

Figure 2:
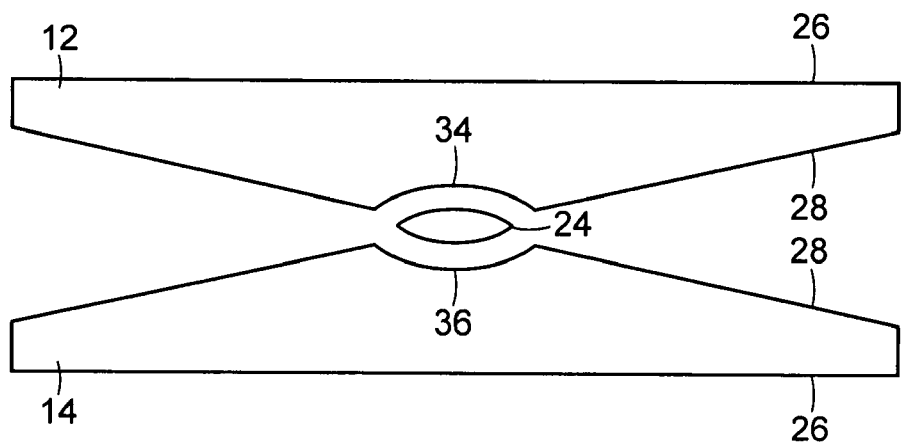
FIG. 2 is a schematic side view of an alternative intervertebral implant with two parallel elongate elements with a separate spacer element, in accordance with one embodiment of the invention.

FIG. 2 is a schematic side view of an alternative intervertebral implant 10 with two parallel elongate elements, with a separate spacer element 24 placed between concave or female mating articulation regions 34, 36 on the upper elongate element 12 and the lower elongate element 14 of the implant 10, respectively. Again, each element of the implant 10 includes a substantially flat vertebral surface 26 and a beveled articular surface 28. As described above, the shape of the vertebral surfaces 26 and articular surfaces 28 of each element can be changed in alternative embodiments of the invention to suit the specific requirements of a given implant 10. The upper elongate element 12 and the lower elongate element 14 can also, in certain embodiments, include projections 16, indentations 22, and/or adhesive substances on its vertebral surfaces 26 and/or sides to better connect the elements to the surrounding vertebrae. In alternative embodiments, the mating articulation regions 34, 36 can include at least one, and possible two, convex protuberances, with the corresponding spacer 24 including matching concave sides to mate with the articulation regions 34, 36 of the upper and lower elements 12, 14.

The spacer element 24 allows the two elements to articulate or pivot with respect to each other, as described above. The spacer 24 can replicate the articulation regions and can be an ellipsoid or other appropriate complimentary shape to the mating articulation regions 34, 36, such as, but not limited to, a ball, biconvex, or biconcave shape. The spacer 24 can be constructed from the same material as the elongate elements of the implant 10, or be constructed from a different material from the surrounding elongate elements. Using a different material for the spacer 24 can, for example, improve the lifespan of the implant 10 or change the friction characteristics of the articulation region to either ease or possibly hinder the relative motion of the two elongate elements.

Figure 3:
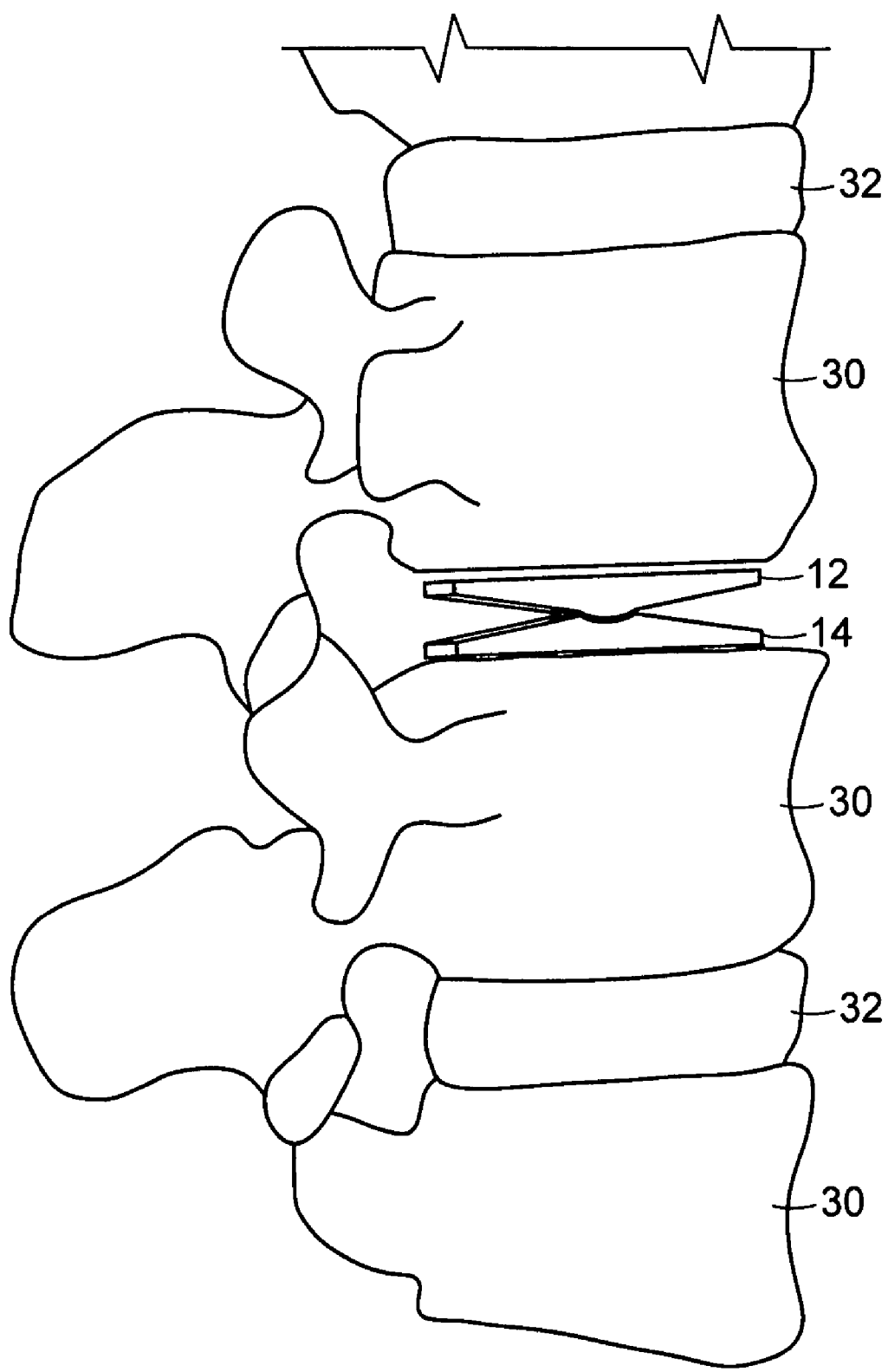
FIG. 3 is a schematic side view of the intervertebral implant of FIG. 1 inserted between two vertebrae, in accordance with one embodiment of the invention.

FIG. 3 is a schematic view of the intervertebral implant of FIG. 1 inserted between two vertebrae. Each vertebra 30 is connected through an intervertebral disc 32. The implant 10 can be used to replace or support an intervertebral disc 32 between two vertebrae 30. As shown in FIG. 3, the vertebral surfaces 26 of the upper elongate element 12 and the lower elongate element 14 rest against the surfaces of the surrounding vertebrae 30. The implant 10 allows the upper 12 and lower 14 elongate elements to articulate relative to each other through the mating articulation region, thus allowing the spine to move and bend in a similar manner to the movement allowed by the healthy intervertebral discs 32.

The implant 10 can be inserted into the intervertebral space in a number of ways, including, but not limited to, a minimally invasive or open lateral, anterior-lateral, or posterior-lateral approach that minimizes soft tissue damage around the implant. FIGS. 4A and 5 show two possible methods for inserting the implant 10 between two vertebrae.

FIG. 4A is a schematic top view of the intervertebral implant 10 of FIG. 1 being inserted into an intervertebral space through a posterior-lateral approach. In this method, because of the small profile of the end of the implant 10, it can be inserted into the intervertebral space through a small incision in the back of the patient. The incision can be made in the back and to the side of the spinal column, for example at an angle of 45 degrees to the front-to-rear axis of the spinal column. In alternative embodiments, this angle can be increased or decreased, depending upon the physiology, size, and shape of the patient and the requirements of the implant 10 upon insertion.

To ease the insertion of the implant into the intervertebral space, a cannula 38, or other appropriate hollow tube, can be inserted into the incision made in the patient's back. The implant 10 can then be inserted through the hollow cannula 38 and into the intervertebral space without having to be forced through the intervening tissue, etc. The insertion of the implant 10 can involve the use of an insertion tool to position the implant 10 at the appropriate location and deploy the positioned implant 10 into is active setting. For example, the implant 10 can be locked in a non-articulating configuration using an inbuilt locking mechanism or a separate locking element. Upon insertion of the implant, this locking mechanism can be released by the insertion tool to allow relative articulation of the upper 12 and lower 14 elongate elements. In alternative embodiments, standard surgical equipment could be used to insert the implant 10 into the intervertebral space, with or without the need for a cannula and/or locking mechanism.

The cannula 38 can be a rigid or flexible tube that can be inserted into the patient through the incision to provide a path for the implant 10. In certain embodiments, this tube can be inserted into the body in its final form, while in other embodiments the tube can be inserted into the body in a collapsed or partially collapsed form to minimize its profile on insertion, and then be expanded to its final form after insertion. The cannula 38 can be a cylindrical, square, rectangular, or other appropriately shaped tube, or it can be shaped to be complimentary to the profile of the implant 10. In some embodiments of the invention, the cannula may have a completely enclosed cross-section, while in other embodiments the cannula can be replaced by an insertion housing 39 that is at least partially open on one side, thus forming a nominally "C" shaped cross-section. The open portion of the insertion housing 39 can, in some embodiments, provide a track that can be used to stabilize the implant during insertion, or to allow bodily matter to exit the channel as the implant 10 is inserted. An end view of an example insertion housing 39 can be seen in FIG. 4B, with a nominally "C" shaped cross-sectional housing 39 providing a hollow central channel 41 for passage of the implant 10, and a gap 43 providing a track for the implant 10 and a means of escape for any matter within the housing 39. Additionally, the cannula 38 or housing 39 can include geometry, such as a wedge shape, at its proximate end within the body to spread adjacent vertebrae apart or otherwise facilitate insertion of the implant.

FIG. 5 is a schematic top view of the intervertebral implant 10 of FIG. 1 being inserted into an intervertebral space through a lateral approach. In this method, an incision is made in the side of the patient at a location resulting in the implant 10 being inserted at an angle of 90 degrees to the front-to-rear axis of the spinal column. The implant 10 can then be inserted into the intervertebral space using any of the same methods and apparatus described for the posterior-lateral approach of FIG. 4A.

Figure 6A:
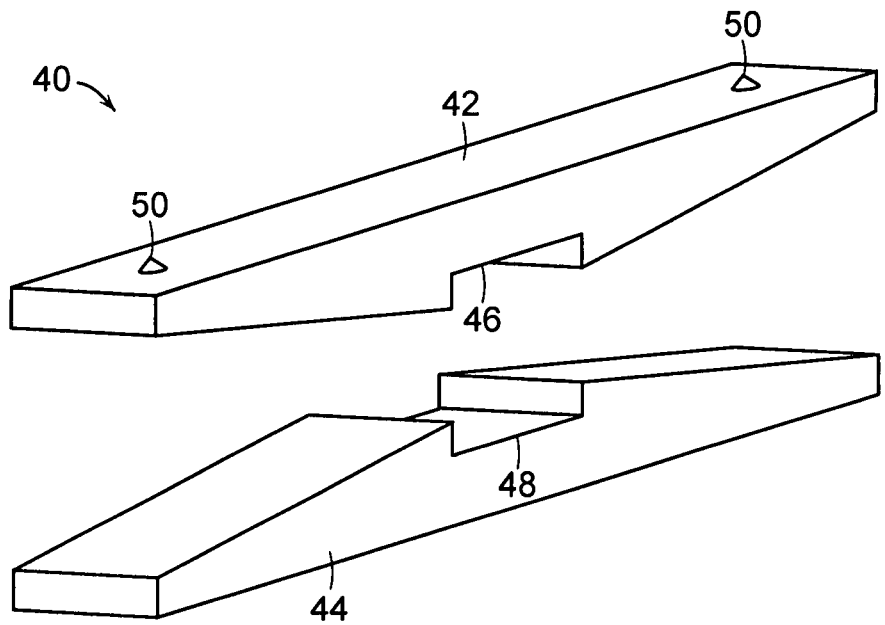
FIG. 6A is a schematic perspective view of two outer segments of a cross-shaped intervertebral implant, in accordance with one embodiment of the invention.

FIG. 6A is a schematic perspective view of two outer segments of a cross-shaped intervertebral implant. In this configuration, the implant 40 consists of four elongate elements that combine to produce an implant 40 configured as upper and lower cross-shaped elements that interact at a central mating articulation region. FIG. 6A shows two outer segments of the implant 40. Here, an upper secondary element 42 and a lower secondary element 44 are positioned parallel to each other. The vertebral surfaces of the elements 42, 44 include protuberances 50 that can be used to more securely connect the implant 40 to the abutting vertebrae. These protuberances 50 can take any of the forms described for the embodiments of FIGS. 1-5. The elements 42, 44 can also include indentations and/or adhesive portions, again as described for the embodiments of FIGS. 1-5.

Figure 6B:
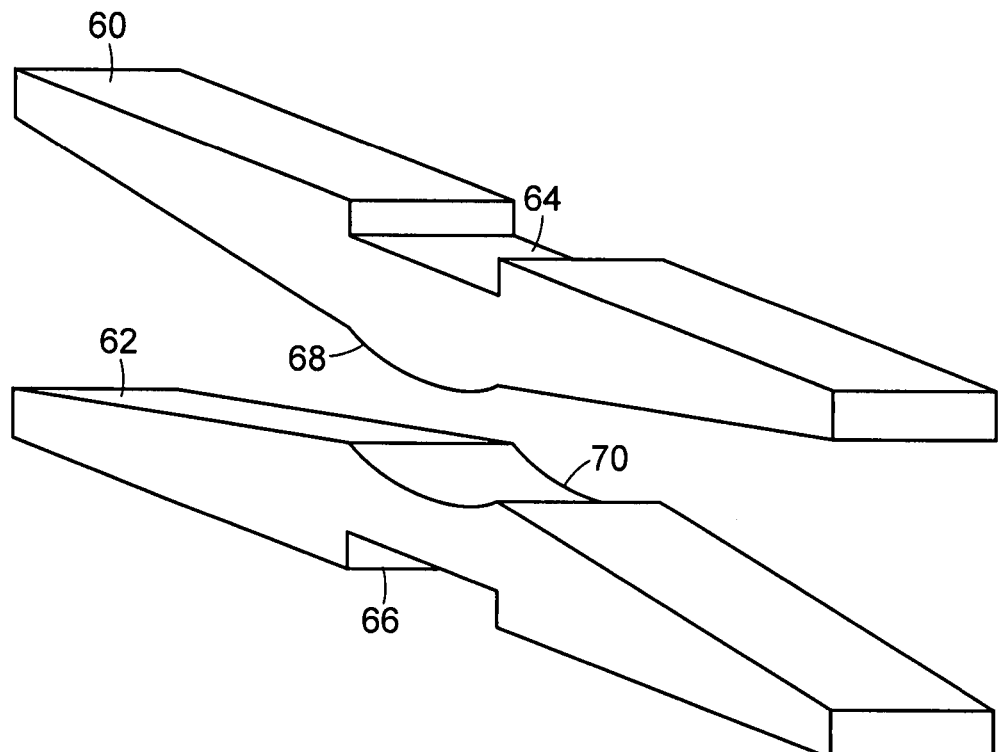
FIG. 6B is a schematic perspective view of two inner segments of a cross-shaped intervertebral implant, in accordance with one embodiment of the invention.

The center of the articular surfaces of each of the elements 42, 44 include notches 46, 48, respectively, allowing the elements 42, 44 to interlock with optional, complimentary notches on the crossing elements of the implant 40. These crossing elements can be seen in FIG. 6B. Here, an upper primary element 60 and a lower primary element 62 are positioned parallel to each other, at 90 degrees to the upper and lower secondary elements 42, 44. The upper and lower primary elements 60, 62 include optional notches 64, 66, respectively, allowing the elements 60, 62 to interlock at 90 degrees to the secondary elements 42, 44 shown in FIG. 6A.

The primary elements 60, 62 also include a mating articulation region allowing the upper element 60 to connect to the lower element 62 in an articulating or pivoting manner. In the embodiment shown, the upper articulation element, attached to the upper element 60, comprises a convex or male protuberance 68, while the lower articulation element, attached to the lower element 62, comprises a corresponding concave or female receptacle 70. As described above for the embodiments of FIGS. 1-5, the mating articulation region may include a number of possible arrangements, such as, but not limited to; a complementary male and female articulation, two female, or one female and one male, or two male articulations with a complementary spacer; a ball and socket articulation; a pair of saddles; or any other appropriate mating elements. As with the embodiments of FIGS. 1-5, the mating articulation can, in certain embodiments, allow articulating or pivoting motion along only one elongate axis, or in other embodiments, allow the implant 40 to pivot in any direction about the central axis of the mating articulation.

The elongate elements 42, 44, 60, 62, are all tapered on their articular surfaces to allow for an increased range of motion as the implant 40 is pivoted or articulated. In certain embodiments, the taper may be equal on each elongate element to allow the implant 40 to pivot equally in each direction. In other embodiments, each elongate element may have a different taper or shape, to increase or decrease the angle at which the implant 40 can pivot in certain directions. For example, the range of motion of a patient's spine is not necessarily equal in all directions, so by careful selection of the shape and taper of each elongate element, the range of motion of two vertebrae with respect to each other can be matched in all directions.

Figure 7:
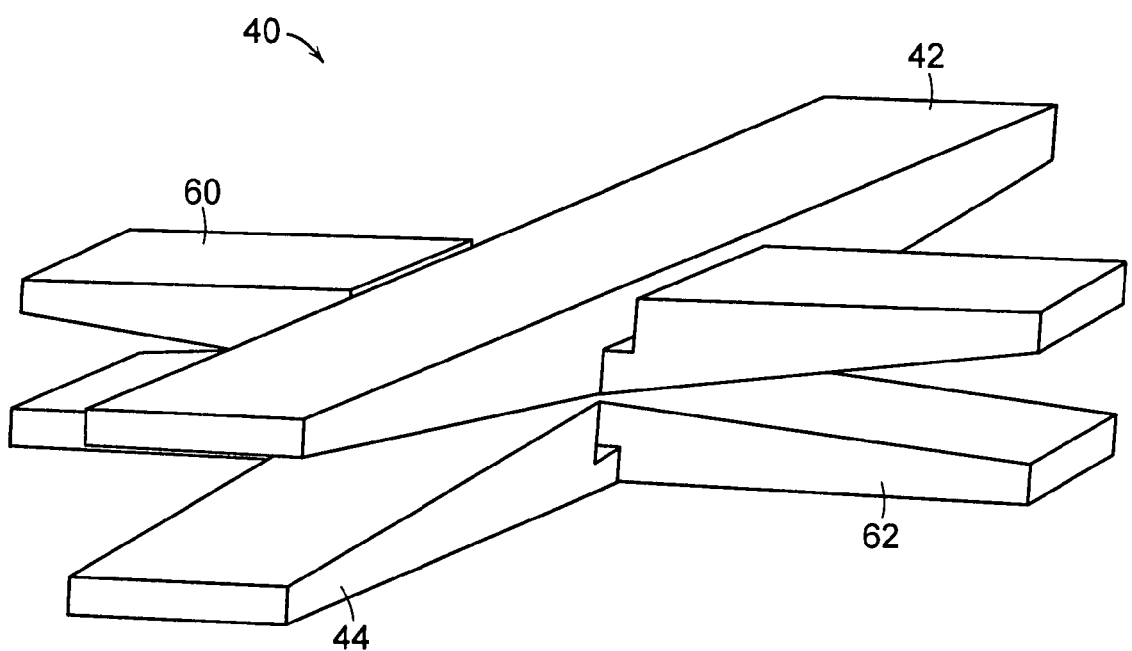
FIG. 7 is a schematic perspective view of an assembled cross-shaped intervertebral implant, in accordance with one embodiment of the invention.

Interlocking upper primary element 60 and secondary element 42 together and lower primary element 62 and secondary element 44 together at the locations of the notches on each element results in the assembled implant 40 shown in FIG. 7. Constructing an implant that forms a cross shape can increase the stability of the implant and allow the upper and lower elements to better pivot in all directions. The cross shape construction also increases the surface area over which the vertebral surface of each element contacts the vertebra. This helps to spread the load between the implant and the associated vertebrae and can thus help to avoid subsistence, wherein the implant sinks or imbeds into the vertebrae over time, possibly damaging the vertebrae.

Figure 8:
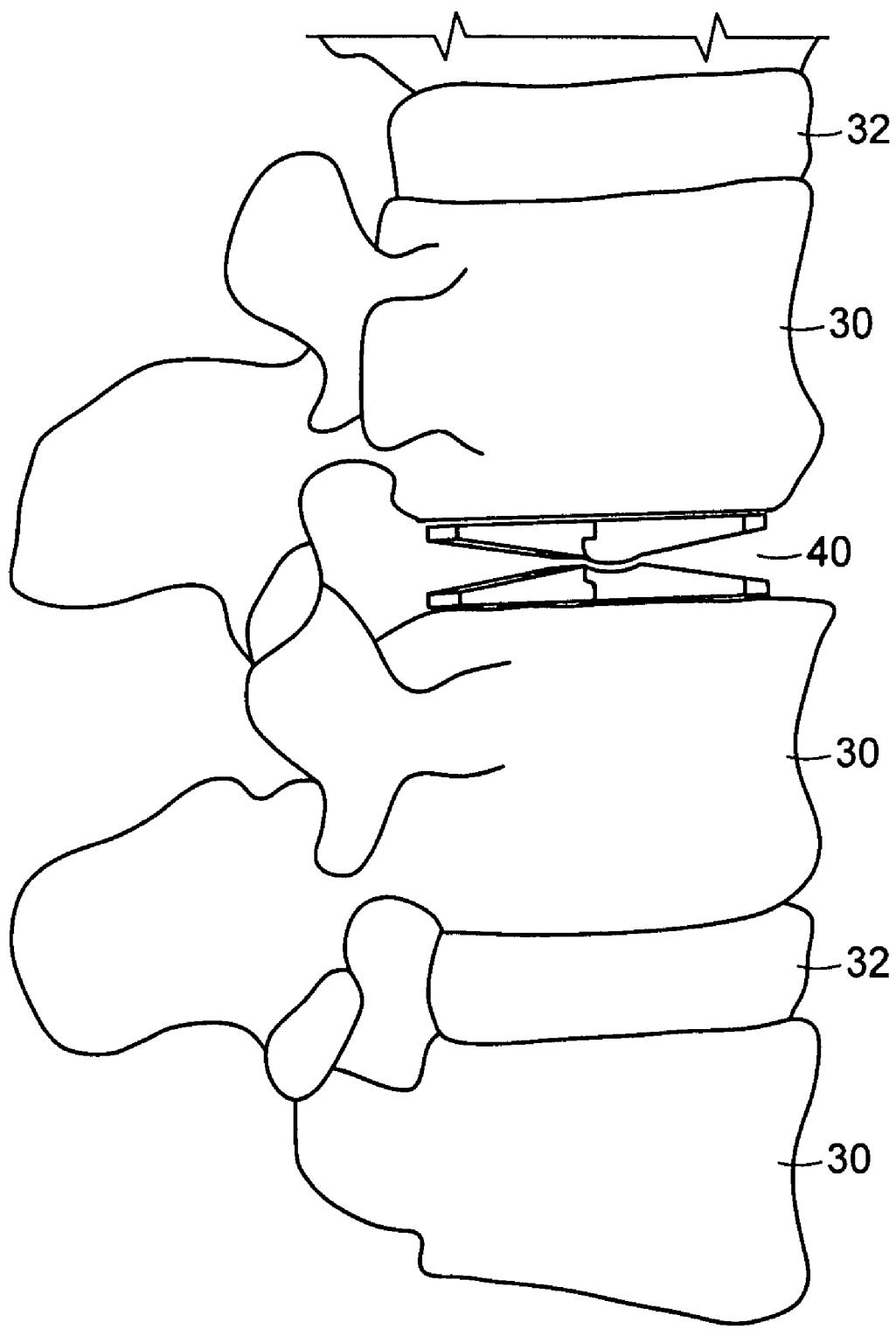
FIG. 8 is a schematic side view of the intervertebral implant of FIG. 7 inserted between two vertebrae.
Figure 9:
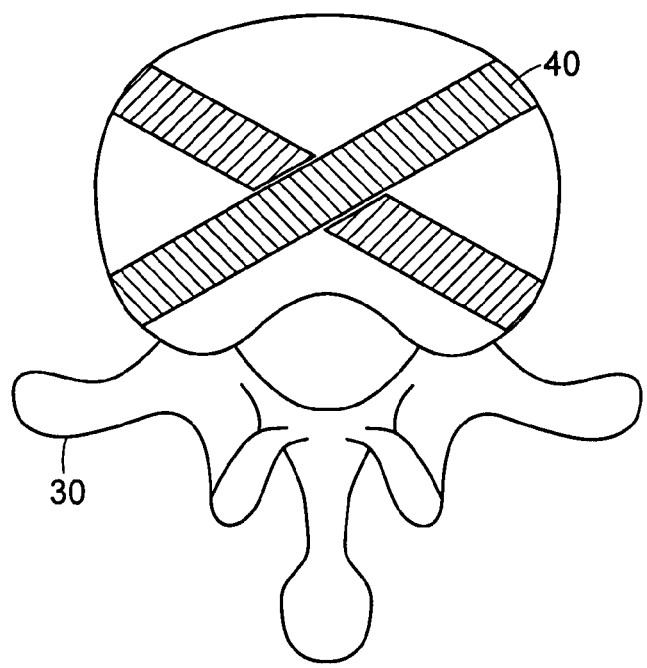
FIG. 9 is a schematic top view of the intervertebral implant of FIG. 7 inserted into a intervertebral space.

An example of a cross-shaped implant inserted within a body can be seen in FIGS. 8 and 9. FIG. 8 depicts a side view of the intervertebral implant 40 inserted in the spinal column, between two vertebrae 30, such that it can replace or support a damaged intervertebral disc at that location. FIG. 9 shows a top view of a cross shaped implant 40 placed between two vertebrae 30. While in some embodiments of the invention, the crossing elements of the implant can be at 90 degrees to each other, in other embodiments, such as in the implant of FIG. 9, the angle between elements of the cross may be smaller than 90 degrees. Implants with different crossing angles may be used depending upon such factors as the geometry and size of the vertebrae being supported and the physiology of the patient.

Due to the larger profile of the cross-shaped implant 40, a larger incision may be necessary in the patient to insert the implant 40 within the intervertebral space. This can be reduced, however, by using an implant that can be inserted into the body in a folded or collapsed configuration to minimize its cross-sectional profile, after which the implant is deployed into a cross-shaped configuration within the intervertebral space. Alternatively, the secondary segments 42, 44, can be inserted in a posterior-lateral approach from one side of the spinal column, while the primary segments 60, 62, are inserted in a posterior-lateral approach from the other side of the spinal column. The primary and secondary elements are then interlocked while in position within the intervertebral space. For example, in one embodiment, the notches in the assembled secondary elements form a tunnel through which the two assembled primary elements can be inserted from the opposite side. This method would mean that only two small incisions would need to be made rather than one large incision.

In another embodiment of the invention, a cross shaped implant 100 can be formed from two single elongated elements 102, 104, that cross at a central mating articulation region. Various embodiments of implant 100 can be seen in FIGS. 10-15. Each elongated element has a vertebral surface with properties as discussed above, and in the embodiment shown the elongated elements includes projections 106. In certain alternative embodiments, the projections 106 can be replaced by, or work in conjunction with, indentations and/or adhesive elements. Again, the elements can be tapered to varying degrees, or the cross-sectional profile of the elements changed, depending upon the specific requirements of the implant 100.

Figure 10:
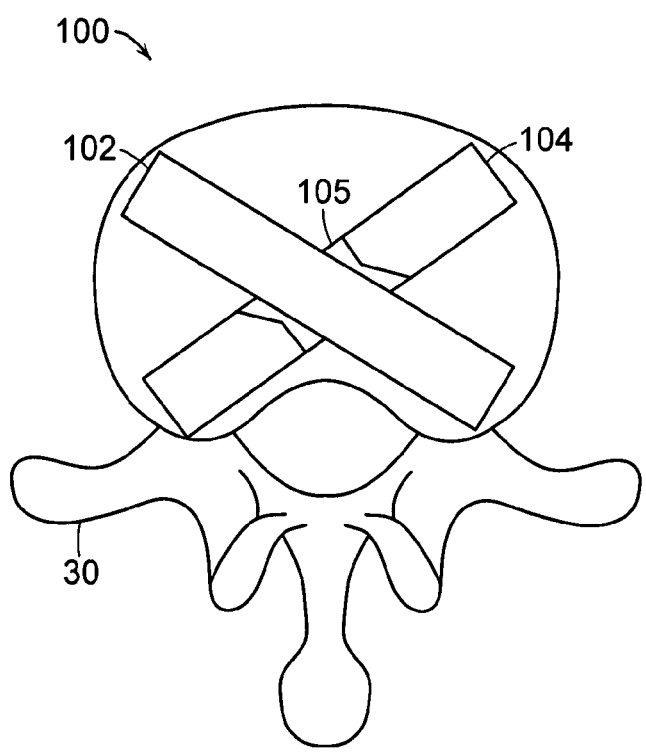
FIG. 10 is a schematic top view of an alternative intervertebral implant, consisting of two crossing elements, inserted into a intervertebral space, in accordance with one embodiment of the invention.
Figure 11:
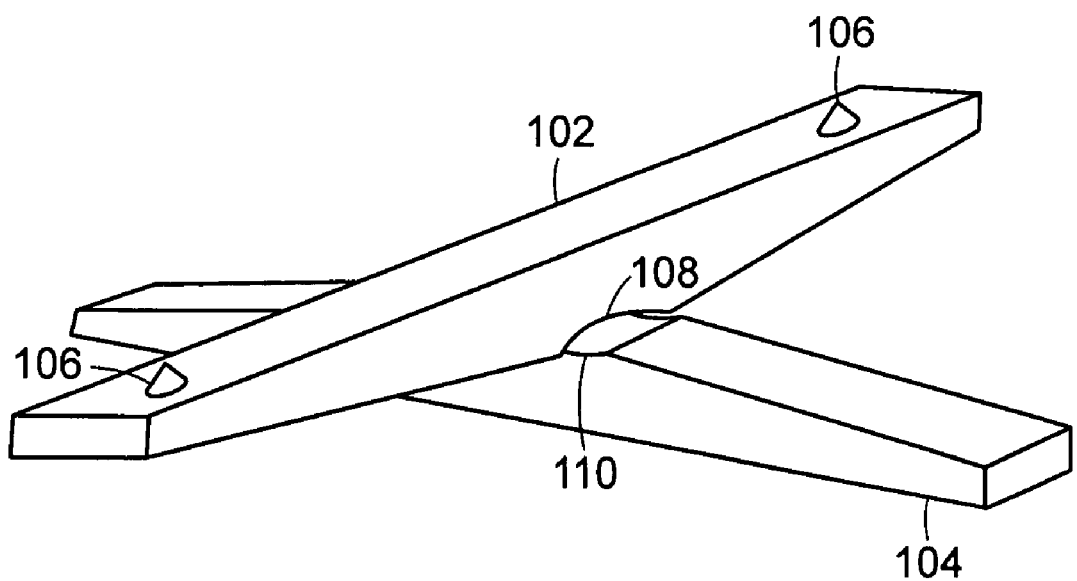
FIG. 11 is a schematic perspective view of the intervertebral implant of FIG. 10.

FIG. 10 shows a top view of the implant 100 inserted in an intervertebral space between adjacent vertebrae 30. The two elements cross at an angle less than 90 degrees, although in alternative embodiments this angle can be increased up to 90 degrees or decreased down towards 0 degrees. As shown in FIG. 11, the upper elongated element 102 and the lower elongated element 104 contact each other at a mating articulation assembly, substantially at the center of the articular surface of each element. The mating articulation includes a saddle shaped surface 108 on the upper element 106, and a corresponding saddle shaped surface 110 on the lower element 104.

The saddle shaped surfaces 108, 110 allow the upper and lower elongated elements 102, 104 to articulate, pivot, twist, or rotate with respect to one another. As can be seen in FIG. 10, the saddle shaped surfaces 108, 110 extend slightly beyond the width of the corresponding element, thus allowing the two elements to twist with respect to each other and increase or decrease the angle between the two elements. This can be advantageous in allowing the spine to twist during motion. In alternative embodiments, the saddle shaped surfaces 108, 110 may fit together with a more snug fit, thereby limiting or stopping twisting of the two elements 102, 104 with respect to each other.

In alternative embodiments of the implant 100, the saddle type mating articulation can be replaced by other appropriate mating articulations, such as, but not limited to, a complementary male and female articulation, two female or male articulations and a complementary spacer, a ball and socket articulation, a pinned connection, or any other appropriate mating elements. As above, this implant 100 can be inserted with a posterior-lateral approach into the intervertebral space though two small incisions, each one in the back of the patient at either side of the spine.

In any of the embodiments of the invention mentioned above or below, the elongated elements may be replaced by spring elements, such as the spring elongated element 120 of FIG. 12, or the arched elongated element 130 shown in FIG. 13.

Figure 12:
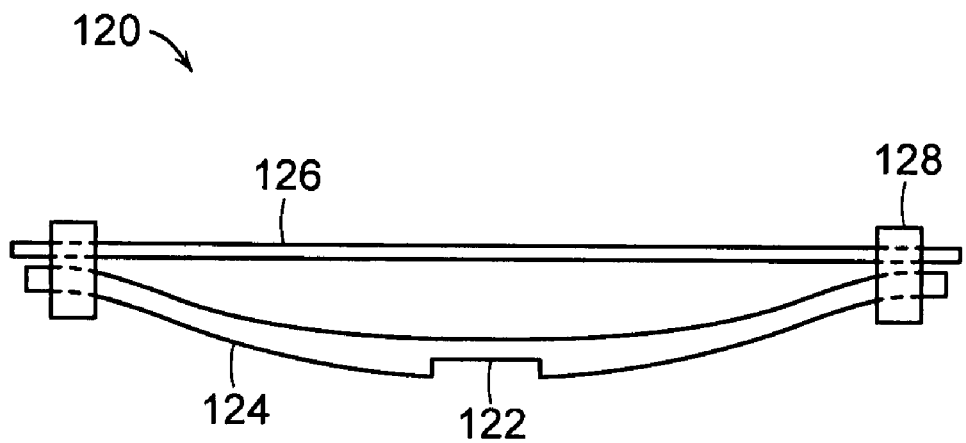
FIG. 12 is a schematic side view of a "leaf-spring" element of an intervertebral implant, in accordance with one embodiment of the invention.

FIG. 12 shows a spring type elongated element 120 consisting of an arched or curved bar 124, a straight or flat bar 126, and connectors 128 holding the two bars together at their outer ends. The configuration can result in the element 120 providing a "leaf spring" effect. The element 120 also includes a notch 122 for mating with another elongated element 120. The use of spring type elongated elements 120 can be advantageous in adding flexibility to the implant, and may, in certain embodiments, relieve the need for articulating connections between the upper and lower elements, with the upper and lower elements instead connected together in a fixed configuration. In this configuration, the required range of motion of the implant can be provided by the spring motion of the elongated elements themselves.

In an alternative embodiment, the notch 122 may be replaced by any of the other mating articulations mentioned above. In some embodiments of the invention, only one, or some, of the elongated elements in a given implant can be spring type elongated elements 120, while in other embodiments, all of the elongated elements in an implant may be spring type elongated elements 120.

Figure 13:
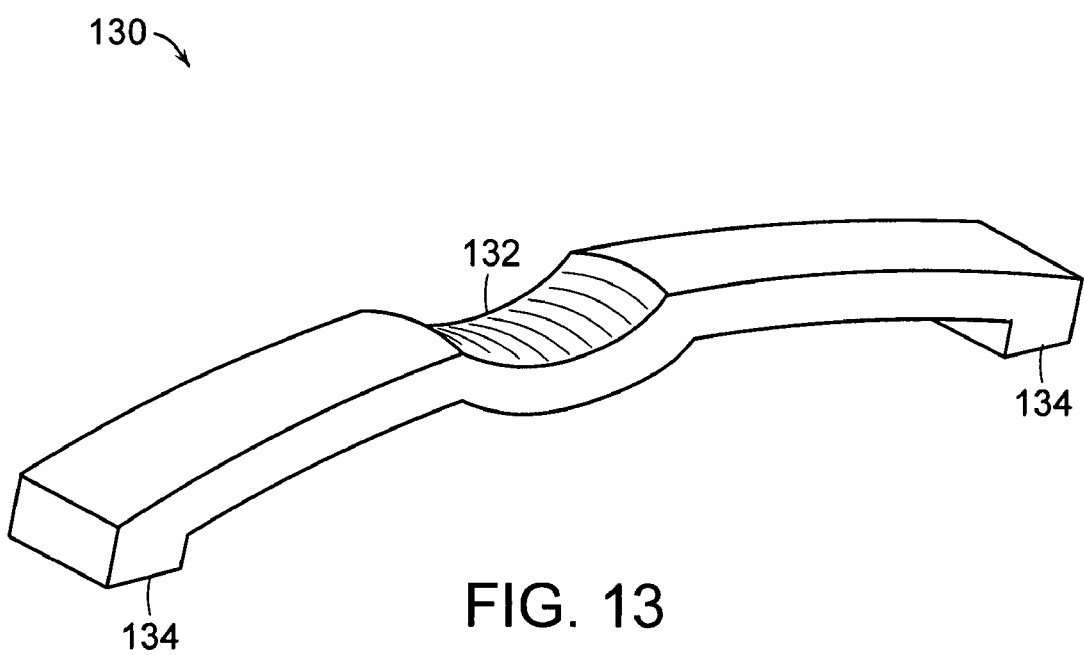
FIG. 13 is a schematic perspective view of an arched element of an intervertebral implant, in accordance with one embodiment of the invention.

FIG. 13 shows an arched elongated element 130 consisting of two end assemblies 134 supporting an arch on which a saddle type mating articulation 132 is located. In alternative embodiments, the saddle 132 can be replaced by any of the other mating articulations or connections described above. As with the spring type elongated element 120 described above, the arched elongated element 130 can provide a "leaf spring" effect that can be advantageous in either increasing the flexibility of the implant or replacing a mating articulation between the upper and lower elements of the implant.

In any of the above or below mentioned embodiments of the invention certain or all of the elongate elements could include a slotted portion on its articular surface. This can be advantageous in providing stability to the implant during use, and/or providing a means of aligning the elements during placement within the intervertebral space. The sides of the slots may, in some embodiments, be tapered or rounded to allow clearance for an axial rotation, or twisting motion, between the upper and lower elements of the implant. For example, the sides of notched or saddled mating articulations could be angled or radiused to provide clearance and enable elements to pivot horizontally with respect to each other, as shown by the angled notches 105 depicted in FIG. 10.

Figure 14:
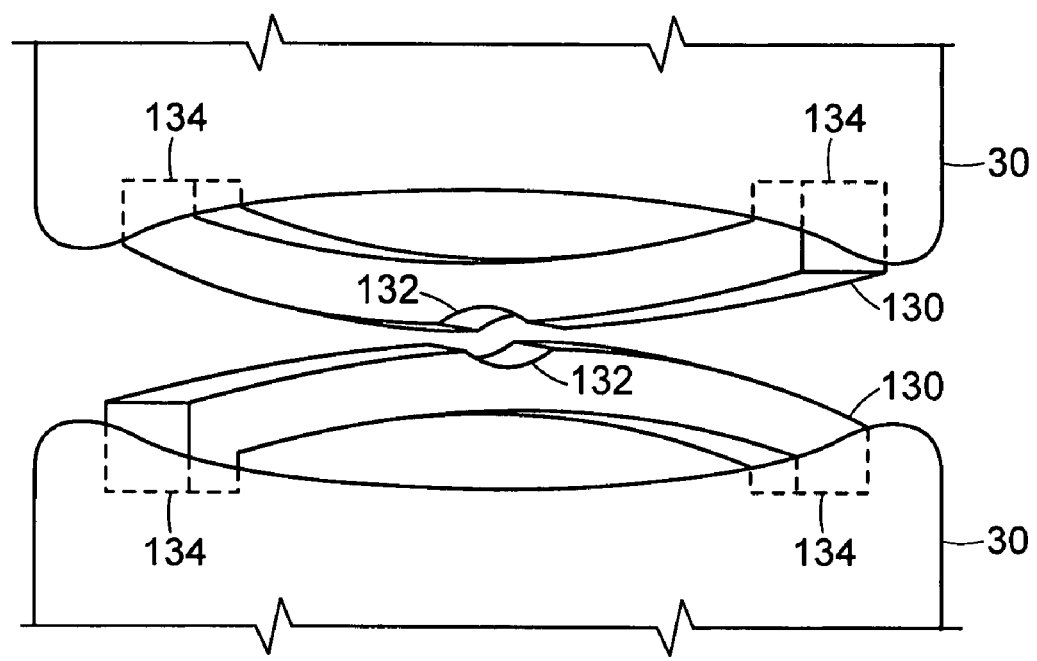
FIG. 14 is a schematic side view of two arched elements inserted between two vertebrae in a crossing configuration.
Figure 15:
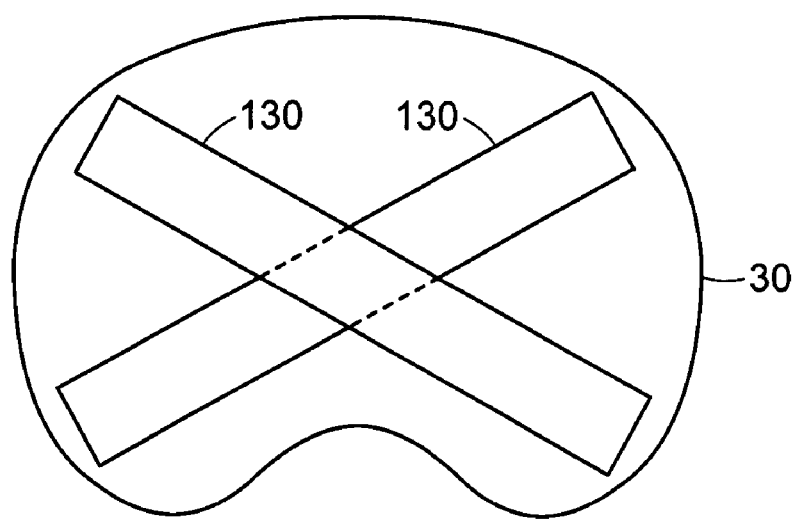
FIG. 15 is a schematic top view of the configuration of FIG. 14.

One embodiment of an implant using arched elongated elements 130 with saddle type mating articulations 132 can be seen in FIG. 14. Here, the implant is shaped in a similar manner to the two element crossing implant 100 of FIGS. 9-10, with the elongated elements 102, 104 replaced by a pair of arched elements 130. The ends 134 of the arched elongated elements 130 are imbedded securely into the abutting vertebrae to secure the implant in place. This imbedding of the ends of the arched elements can be achieved either surgically at the time of insertion or happen naturally over time due to subsidence caused by the pressure exerted on the implant by the spine. A top view of the cross type implant with arched elongated elements 130 can be seen in FIG. 15.

An embodiment of an implant 140 using arched elongated elements 130 with a complementary male 142 and female 144 articulation can be seen in FIG. 16. In this configuration, two parallel arched elongated elements 130 replace the elongated elements 12, 14, from the embodiments of FIGS. 1-5. Using the parallel configuration can allow the implant to be inserted into the intervertebral space using a single incision.

Another embodiment of the invention can employ a scissors type design, with two elongated elements connected together by a pin-type connection. In this embodiment, the elements of the implant can be placed parallel during insertion to minimize the implant's cross sectional profile during insertion, but then be opened after insertion to form a crossing type configuration. This embodiment can be employed for both a two element crossing configuration and a four element crossing configuration. The scissors type configuration allows a single implant to be deployed with any required angle from about 0 degrees to about 180 degrees between the separate elongate elements of the implant. A scissors type implant is also advantageous in that it allows a crossing implant to be inserted through a single incision in the patients back, rather than requiring two incisions on either side of the spine as described above. In certain embodiments, the pin-type connection can include an elastic pin, or an attachment of another suitable pliable material, thus allowing the pinned connection to bend and thus allow relative articulation of the upper and lower elements about the connection location.

FIGS. 17A and 17B show a two element scissors type implant 150 in an insertion and deployed configuration, respectively. The implant 150 includes an upper elongate element 154 and a lower elongate element 156. These two elements 154, 156, are connected by a pin 152 through the center of each element. The implant 150 can be inserted into the intervertebral space in its closed or insertion configuration, as shown in FIG. 17A, where it has a small cross-sectional profile and, therefore, can minimize the damage to soft tissue during insertion. Upon placement within the intervertebral space, the implant 150 can be deployed into its opened configuration, as shown in FIG. 17B. In some embodiments of the invention, a specially designed insertion tool can be used to insert and deploy the implant 150, while in an alternative configuration, a standard surgical tool can be used to insert and deploy the implant 150. The elements of the implant 150 can be made from two tapered elements, as described for the embodiments of FIGS. 1-11, while in an alternative embodiment, arched elongated elements may be used.

In alternative configurations, the pin 152 can be replaced by any of the mating articulations described previously, such as but not limited to, a complementary male and female articulation, two female or male articulations with a complementary spacer, a ball and socket articulation, a pair of saddles, or any other appropriate mating elements. For a scissors type implant with one of these mating articulations to be inserted through a single incision, there may be the need for an insertion tool to hold the pieces together during insertion.

An embodiment of the invention including a four arm scissors type implant 200 can be seen in FIGS. 18-22. In this embodiment, an upper scissors assembly 202 mates to a lower scissors assembly 204 through a mating articulation 206. Both the upper 202 and lower 204 scissors assemblies include two separate elongated elements that can be connected through a pivot, pin, or other appropriate connection to form single scissors assemblies that can rotate relative to each other about the center of each element. The mating articulation 206 includes a ball and socket articulation. In alternative embodiments of the invention, other mating articulations, such as those mentioned above, can be employed in place of the ball and socket 206.

The implant 200 can, in certain embodiments, include any feature, or group of features, discussed in the previously mentioned embodiments of the invention, including but not limited to, projections on the vertebral surfaces, indentations, adhesive sections, variably tapered, curved or flat elongate elements, and arched or spring elements.

Figure 18:
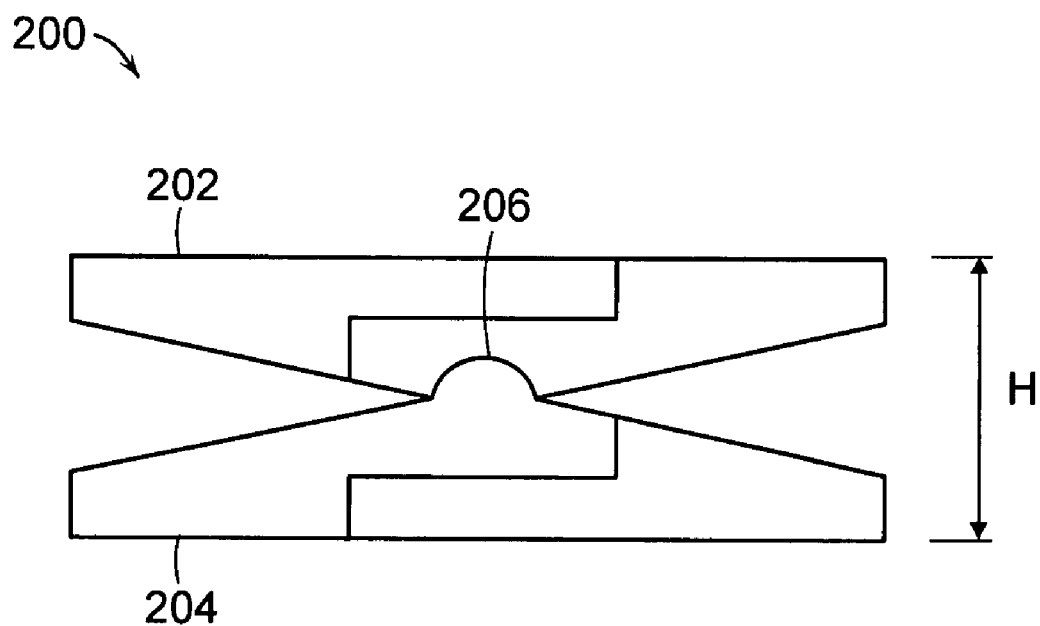
FIG. 18 is a schematic side view of a four segment "scissors" type intervertebral implant in a closed configuration, in accordance with one embodiment of the invention.

FIG. 18 shows a side view of the implant 200 in a closed or insertion configuration. A corresponding top view of the closed configuration can be seen in FIG. 19, looking down on the upper scissors assembly 202. Side and top views of the implant 200 in an open or deployed configuration can be seen in FIGS. 20 and 21, respectively.

Figure 19:
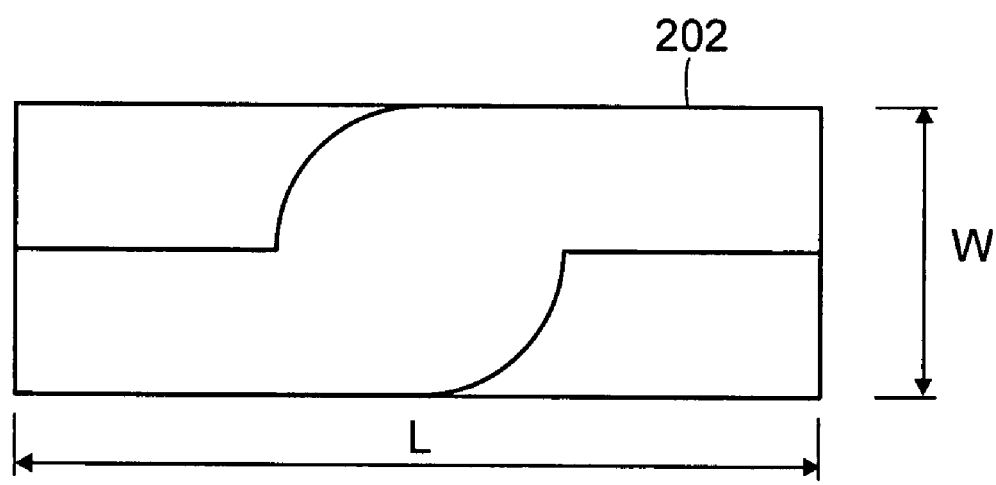
FIG. 19 is a schematic top view of the closed four segment "scissors" type intervertebral implant of FIG. 18.
Figure 20:
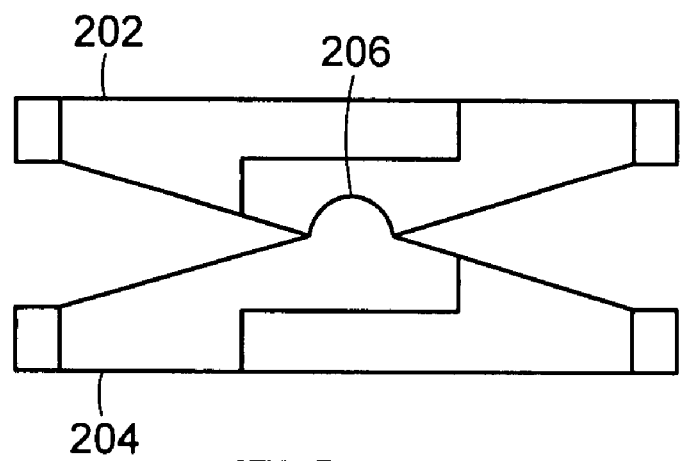
FIG. 20 is a schematic side view of a four segment "scissors" type intervertebral implant in an open configuration, in accordance with one embodiment of the invention.
Figure 21:
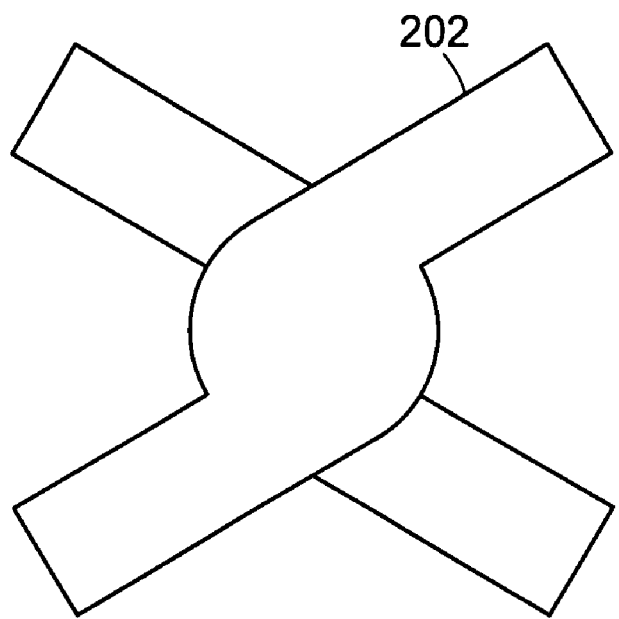
FIG. 21 is a schematic top view of the open four segment "scissors" type intervertebral implant of FIG. 20.

Each of the upper scissors assembly 202 and the lower scissors assembly 204 includes two elongated elements that are pivotably connected about their central region. The portions of the elements extending out from the central region of each element are offset from the central lengthwise axis of the element, with the offset of one element of each assembly mirroring the offset of the other element of that assembly. As a result, the two elements of each assembly can pivot together into a closed configuration such that they form a single flat surface, as seen in FIGS. 18 and 19. This produces a substantially flat vertebral surface for both the upper scissors assembly 202 and the lower scissors assembly 204. Upon deployment of the implant, the extended portions of each element of each assembly rotate about the pivotable connection at the central region of that assembly while maintaining a substantially flat vertebral surface for each assembly, as shown in FIGS. 20 and 21.

In an alternative embodiment of the invention, the scissors elements of each assembly can be configured such that the extended portions of one element pivots below the extended portions of the other element of that assembly, thus lowering the cross-sectional profile of the implant when being inserted. In this embodiment, the scissors elements can include notches or other indentations, such that when being deployed a notch in the upper surface of the inner element matches with a notch on the lower surface of the upper element to allow the vertebral surfaces to be configured as one flat surface. In a further alternative embodiment, this notch may not be included.

Figure 22:
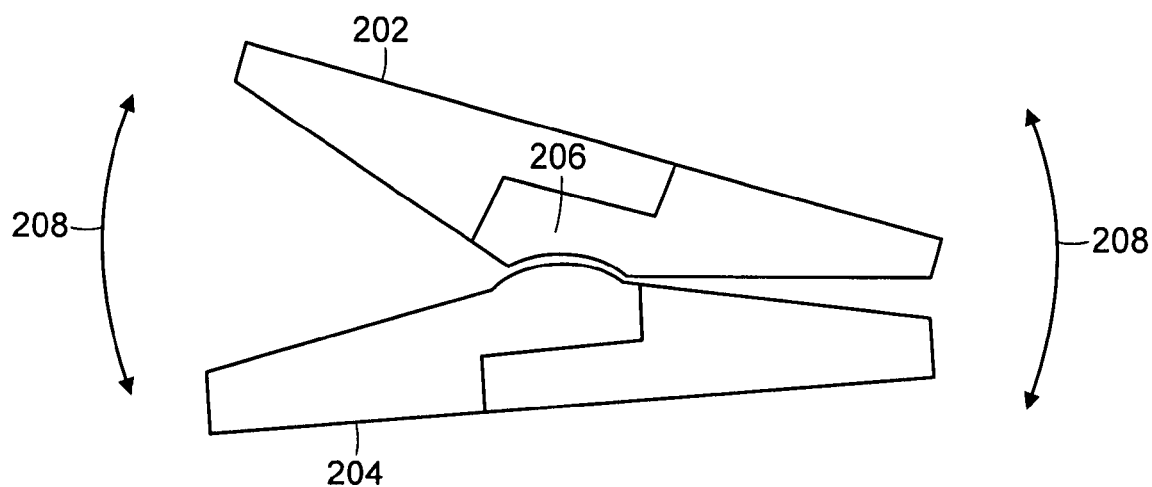
FIG. 22 is a schematic side view of a four segment "scissors" type intervertebral implant articulating about its central axis, in accordance with one embodiment of the invention.

FIG. 22 shows a side view of the implant 200 articulating about its central mating articulation 206. The complimentary articulating surfaces of the upper 202 and lower 204 scissors assemblies allow the upper 202 and lower 204 assemblies to move relative to each other with physiological motion. In terms of spinal motion, the articulation will allow rotation, flexion, extension, lateral bending, and in some embodiments, physiological translation. Some degree of constraint to the translation in one or more direction may be allowed depending upon the shape of the articular surfaces. For example, tapering an elongate element less will limit the range of rotatable motion with respect to that element. Arrows 208 show one example of relative motion of the upper 202 and lower 204 scissors assemblies. As the upper 202 and lower 204 scissors assemblies are separate pieces, an insertion or implantation tool may be necessary in some embodiments to allow the upper 202 and lower 204 scissors assemblies to be inserted together as a single assembly.

FIGS. 23-26 show a top, left-side, right-side, and end view respectively of the implant 200 attached to one embodiment of an insertion tool 220. The insertion tool includes a first or main body 222 and a second or "dummy" support body 224.

The two bodies 222, 224, are connected by a tongue and groove interface 226, allowing the dummy support body 224 to slide along the length of the main body 222. In an alternative embodiment, tracks or other appropriate means of slidably connecting the main 222 and dummy support 224 bodies may replace the tongue and groove interface 226.

The insertion tool 220 can be releasably fixed to the implant 200 through a set of four screws 228 that are inserted through clearance of threaded holes 234 in the two bodies 222, 224 of the insertion tool 220 and screw into threaded holes in the distal ends of the four elongate elements of the implant 200. The screws 228 may be turned through an Allen-key, flat-head or Phillips-head screwdriver, or other appropriate means. In alternative embodiments, the screw attachments between the insertion tool 220 and the implant 200 may be replaced by other appropriate releasable connections, such as, but not limited to, latches, key locks, or magnetic connections.

The distal ends of the main body 222 and the dummy support body 224 have a wedge shaped protrusion 230 that mates with the gap in the sides of the implant 200 due to the tapering of the articular surfaces of the upper 202 and lower 204 scissors elements. In alternative embodiments of the invention, the distal ends of the main body 222 and dummy support body 224 may have flat ends, leaving a gap between the end of the insertion tool 220 and the interior portion of the implant 200.

The main body 222 and the dummy support body 224 both have two screw holes 234. The main body 222 is therefore connected through these two holes 234 to one distal end of an elongate element of both the upper 202 and lower 204 scissors assembly of the implant 200. Thus, the two halves of the implant 200 can be held together using only the main body 222 of the insertion tool 220. The other two distal ends of the elongate elements of the implant 200 can be affixed to the dummy support body 224 of the insertion tool 220, thus further supporting the implant 200 and preventing the scissors assemblies of the implant 200 from opening. Thus, the insertion tool 220 and implant 200 form a single assembly that can be used for storing the implant 200 prior to insertion and for inserting and deploying the implant 200 within the intervertebral space.

A handle 232 is attached to the main body 222 of the insertion tool 220 to aid in the insertion of the implant 200. This handle 222 may be permanently attached to the insertion tool 220 or releasably attached to the tool. In alternative embodiments, the handle 222 may be able to fold into the main body 222 when not in use. The handle 222 may be formed from a simple shape, such as, but not limited to, cylindrical, rectangular, or other polygonal shape. In alternative embodiments, the handle 222 may be formed from a more ergonomically designed shape with, for example, holes or grips to aid the user's holding of the handle 222.

The implant 200 can be inserted into the intervertebral space through a single incision in the back or side of the patient, using the posterior-lateral or lateral approaches described previously. A channel shaped insertion housing or cannula can be employed to ease the insertion of the implant 200 into the body, although in some embodiments, an insertion housing may not be needed. Once correctly positioned within the intervertebral space, the insertion tool 220 can be used to deploy the implant 200 into its working configuration before releasing the implant 200 and being removed.

Figure 28:
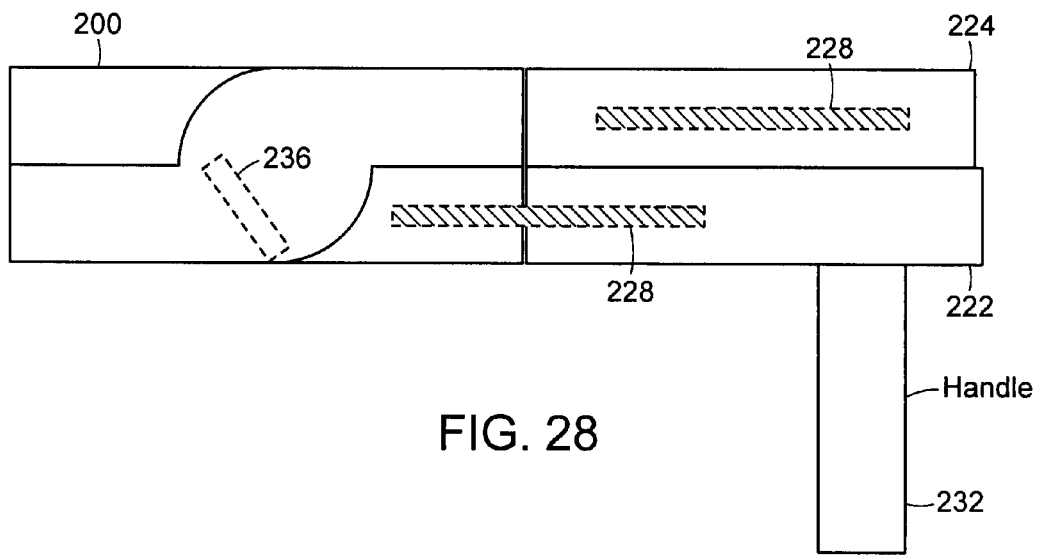
FIG. 28 is a schematic top view of the intervertebral implant and insertion tool of FIG. 27 with the right side attachment screws detached from the implant.
Figure 27:
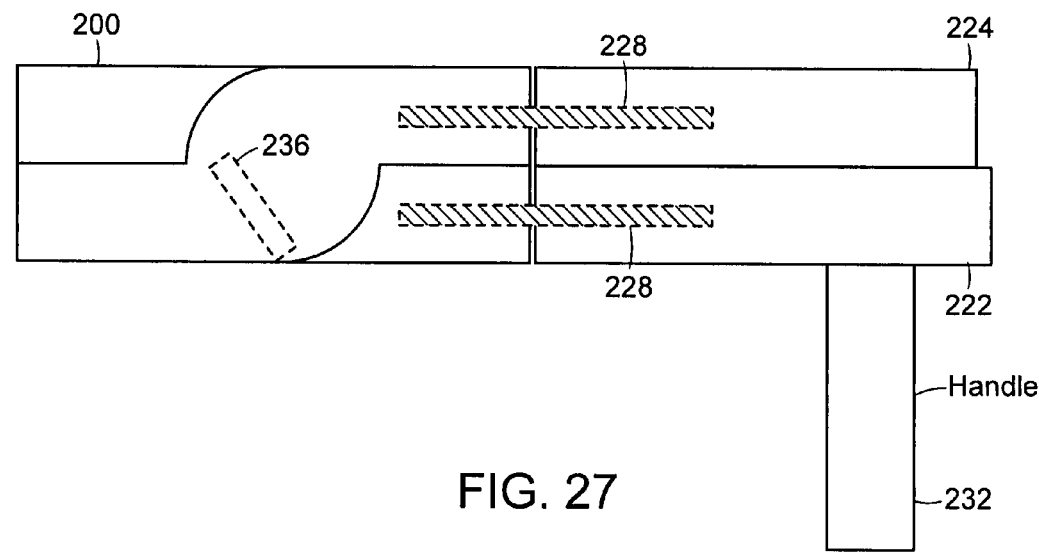
FIG. 27 is a schematic top view of a four segment "scissors" type intervertebral implant mounted on an insertion tool with all attachment screws in place, in accordance with one embodiment of the invention.
Figure 29:
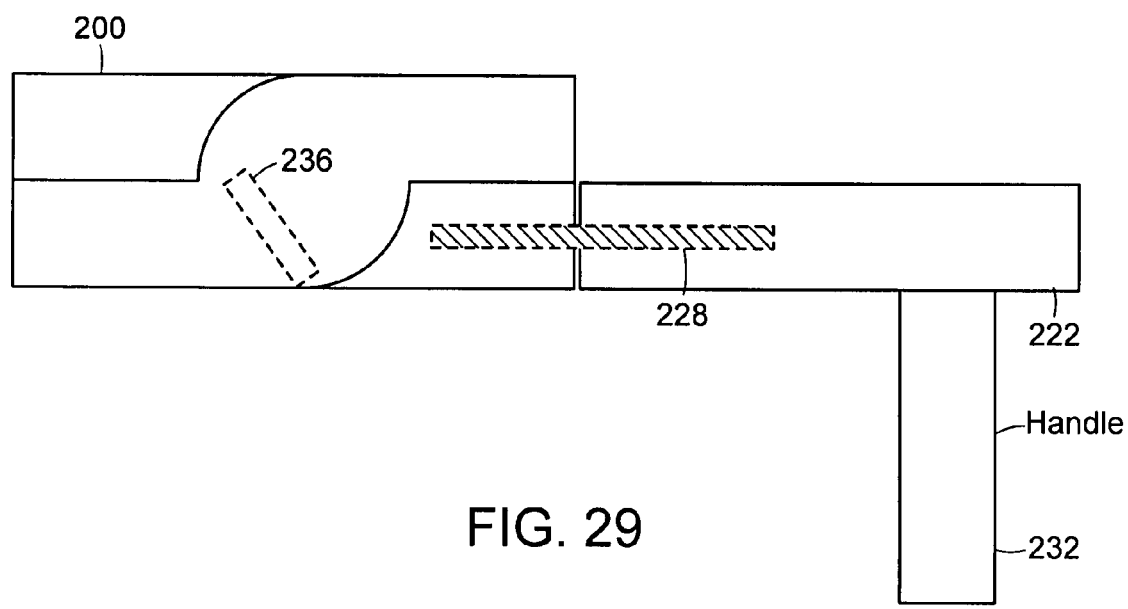
FIG. 29 is a schematic top view of the intervertebral implant and insertion tool of FIG. 27 with the right side of the insertion tool removed.

FIGS. 27-34 show the stages of deployment of the implant 200 after insertion into the intervertebral space by the insertion tool 220. FIG. 27 shows a top view of the implant 200 and insertion tool 220 in its fully connected insertion configuration. Here, all four screws 228 are in place, connecting both the main body 222 and the dummy support body 224 to the implant 200. Once correctly inserted, the two screws 228 within the dummy support body 224 are removed, as shown in FIG. 28. The dummy support body 224 can then be removed by sliding the body 224 out along the tongue and groove sliding connection linking the dummy support body 224 to the main body 222, as shown in FIG. 29.

Figure 30:
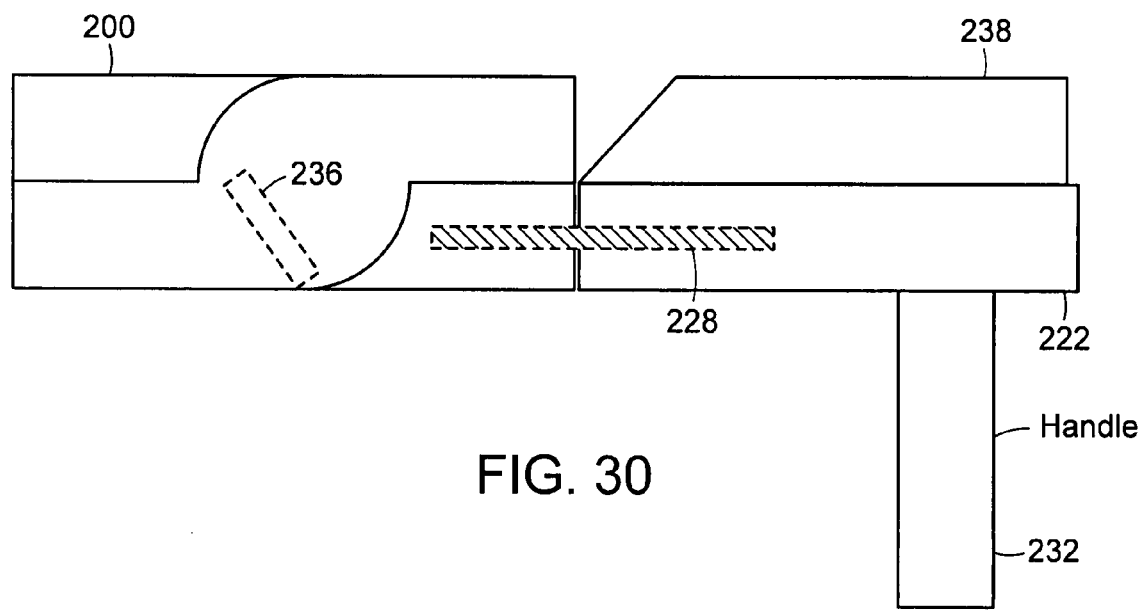
FIG. 30 is a schematic top view of the intervertebral implant and insertion tool of FIG. 27 with the right side of the insertion tool attached in a deployment configuration.

A distracter wedge 238 can then be slid into place along the sliding connection on the main body 222, as shown in FIG. 30. This wedge shaped body 238 can be a separate piece with a wedge shaped distal end set at a predetermined angle, dependent upon the required angle at which the implant 200 is to be deployed. Selecting a distracter wedge 238 with a different angle of wedge at its distal end will result in a different deployment angle for the implant 200. In certain embodiments, the distracter wedge 238 can have a variable distal end, allowing a single piece to be used to deploy the implant 200 at any required angle. In an alternative embodiment, the dummy support body 224 can have a wedge shaped distal end, allowing it to act as the distracter wedge 238, thus alleviating the need for a separate piece to be used to deploy the implant 200. For example, the dummy support body 224 can have a wedge shape at the end furthest from the implant 200 throughout insertion. Then, the dummy support body 224 can be removed, as described in FIGS. 27-29, turned around, and reinserted with the wedge end towards the implant 200.

Figure 32:
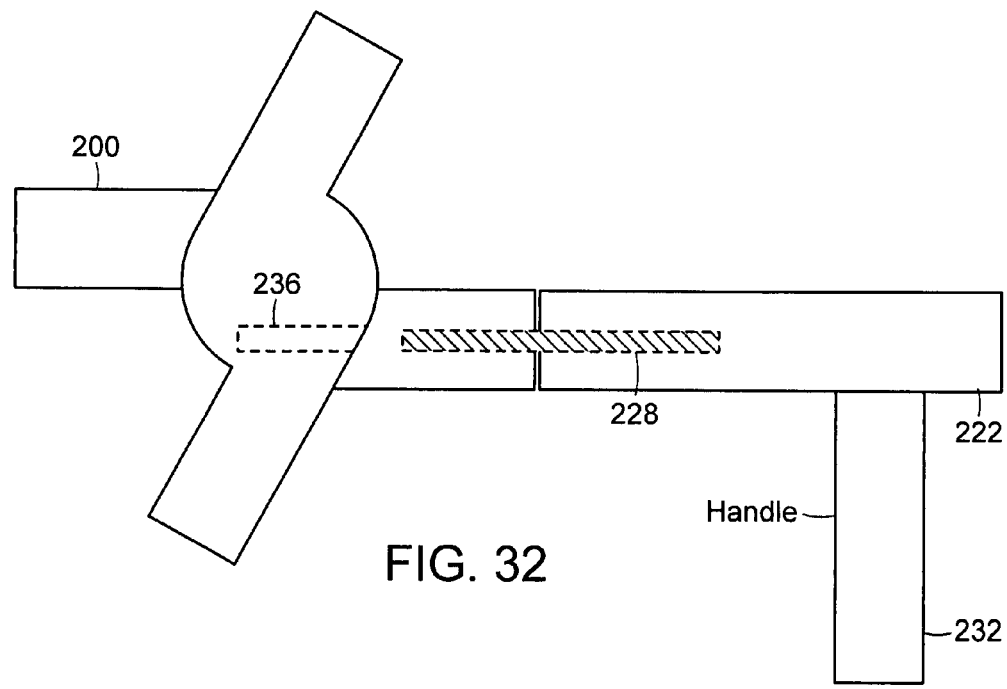
FIG. 32 is a schematic top view of the intervertebral implant and insertion tool of FIG. 27 with the right side of the insertion tool removed and the implant in an opened configuration.
Figure 31:
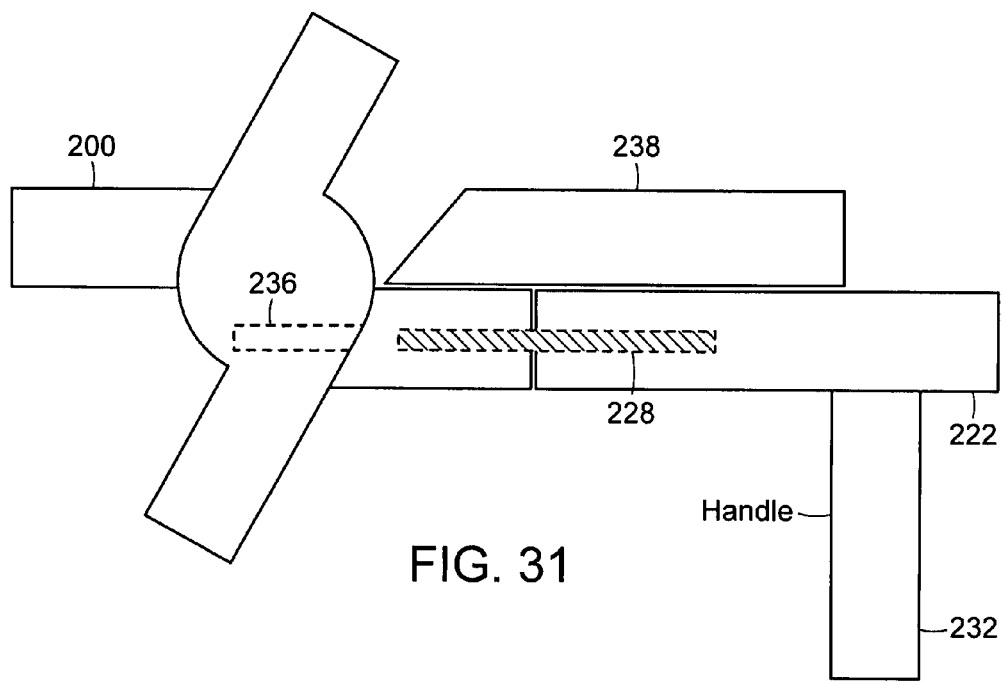
FIG. 31 is a schematic top view of the intervertebral implant and insertion tool of FIG. 27 with the right side of the insertion tool advanced to deploy the segments of the implant.

The distracter wedge 238 can then be advanced forward along the sliding mechanism to engage with the elongate elements of the scissors implant 200, as shown in FIG. 31. After the distracter wedge 238 has been advanced as far as it can go, thus setting the deployment angle of the scissors type elongate elements of the implant 200 to the angle predetermined by the angle and size of the wedge, the distracter wedge 238 can then be removed, as shown in FIG. 32. In certain embodiments, the distracter wedge 238 can be configured to set both the upper and lower scissors assemblies of the implant 200 to the same deployment angle, while in alternative configurations, the distracter wedge 238 can be configured to set the upper and lower assemblies to different deployment angles by having a different geometry for the portion of the distracter wedge 238 contacting each assembly.

Deployment of the implant 200 may be effected by other means, such as, but not limited to, mechanical means, springs, electrical means, or other appropriate means. In certain embodiments, the implant may be constructed from a shape memory material, such as a heat dependent polymer. The implant can be cast in its deployed configuration and then formed into a collapsed state and cooled down, such that while the temperature remains constant, the polymer maintains the collapsed configuration. The implant can then be inserted into the intervertebral space in its collapsed state, at which time body heat will heat the implant and allow the polymer to expand back to its original deployed configuration. A heat dependent polymer could also be inserted in only a portion of the implant 200 to act as a spring, such that the implant 200 can configured in a collapsed configuration for insertion, but once inserted, body heat results in the expansion of the polymer element inserted between the elongated elements of one or both assemblies. This polymer element can then deploy the elongated elements of the implant and lock them in place.

In another example, a spring and latch arrangement could be included in the implant such that upon release of a latch or pin, for example by a wire or other connection through the main body 222 of the insertion tool, the spring forces open the scissors elements to the required angle. In these embodiments, there may not be any need for a distracter wedge 238 or even a dummy support body 224. A piston type element could also be used, in certain embodiments, to deploy the implant 200.

Figure 33:
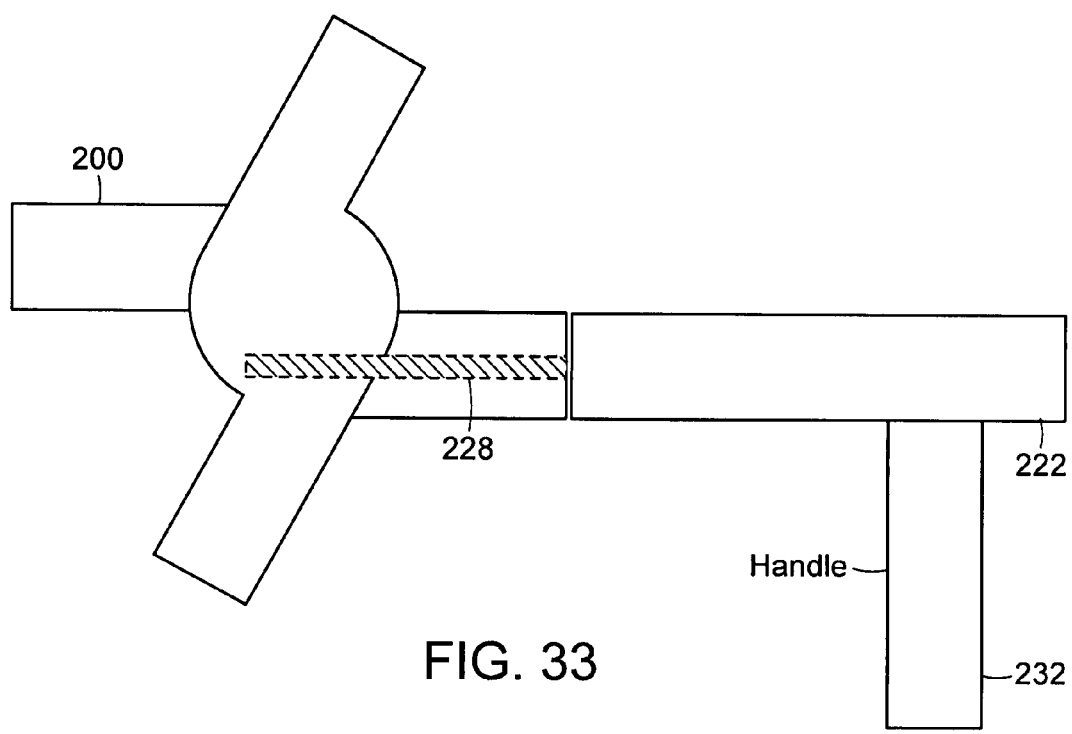
FIG. 33 is a schematic top view of the opened intervertebral implant and insertion tool of FIG. 27 with the attachment screws detached from the insertion tool.

The implant 200 can then be locked into its deployed configuration to prevent it from moving while in use. This can be achieved in one embodiment by threading the screws 228 connecting the main body 222 to the implant 200 into locking holes 236 inserted into both the upper and lower scissors elements of the implant 200, as shown in FIG. 33. These locking holes 236 can be either threaded or non-threaded holes placed within the implant 200 such that they mate with the threaded holes in the elongate elements of the implant 200 when the required deployment angle is set. In some embodiments of the invention the implant 200 can be locked into its deployed position using another locking mechanism, such as, but not limited to, a pin, a latch, or a key lock mechanism. In further embodiments, there may be no locking mechanism for the implant 200, with the force exerted on the implant 200 by the surrounding vertebrae, or the use of projections, indentations, and/or adhesive being enough to hold the implant 200 in position.

Figure 34:
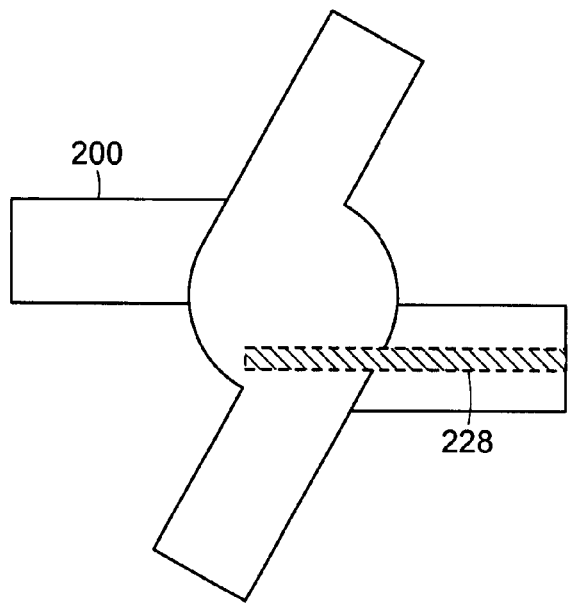
FIG. 34 is a schematic top view of the intervertebral implant of FIG. 27 in the opened and locked position with the insertion tool removed.

Once the screws 228 have been inserted into the implant 200 and no longer connect the implant 200 to the main body 222 of the insertion tool 220, the main body 222 can be removed, leaving the implant 200 in place within the intervertebral space, as shown in FIG. 34. In embodiments that include an insertion channel or cannula, this will also be removed at this time.

Figure 25:
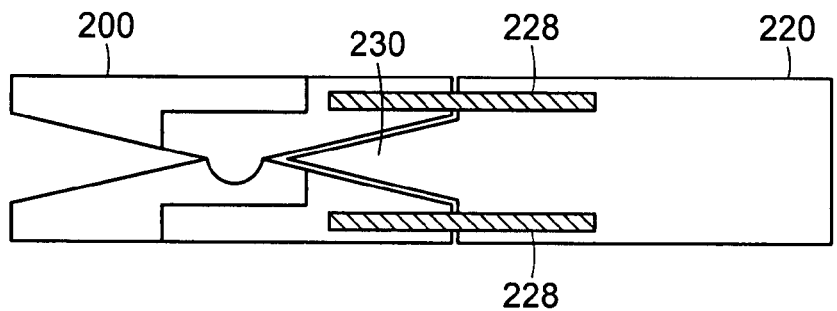
FIG. 25 is a schematic right side view of the intervertebral implant and insertion tool of FIG. 23.
Figure 24:
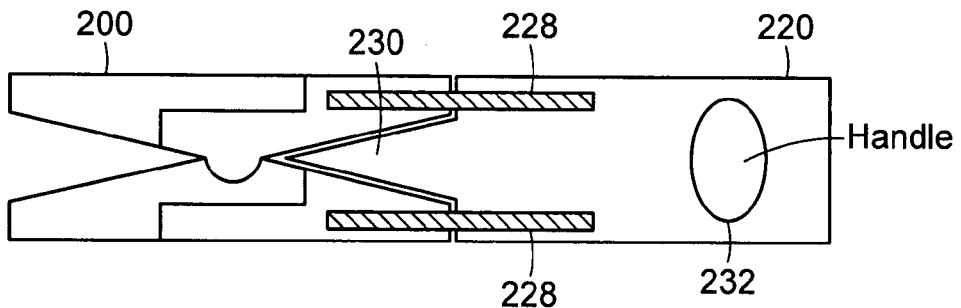
FIG. 24 is a schematic left side view of the intervertebral implant and insertion tool of FIG. 23.
Figure 23:
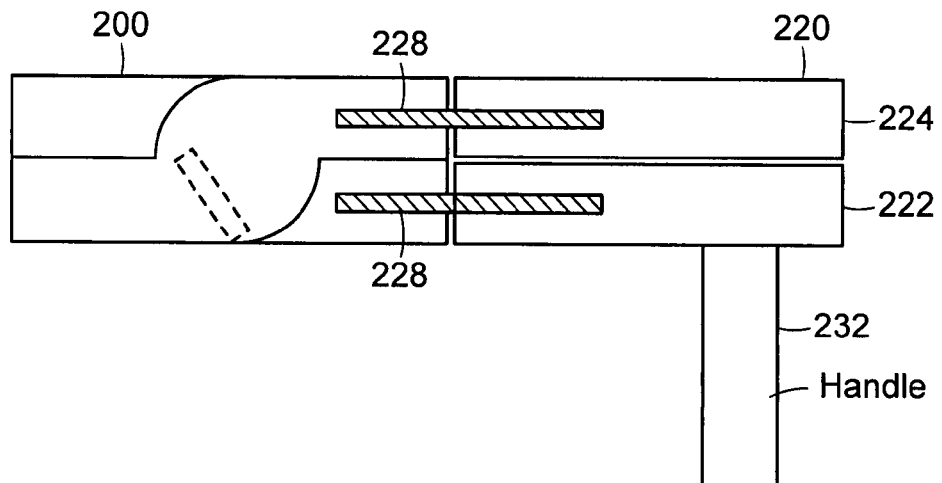
FIG. 23 is a schematic top view of a four segment "scissors" type intervertebral implant mounted on an insertion tool, in accordance with one embodiment of the invention.
Figure 26:
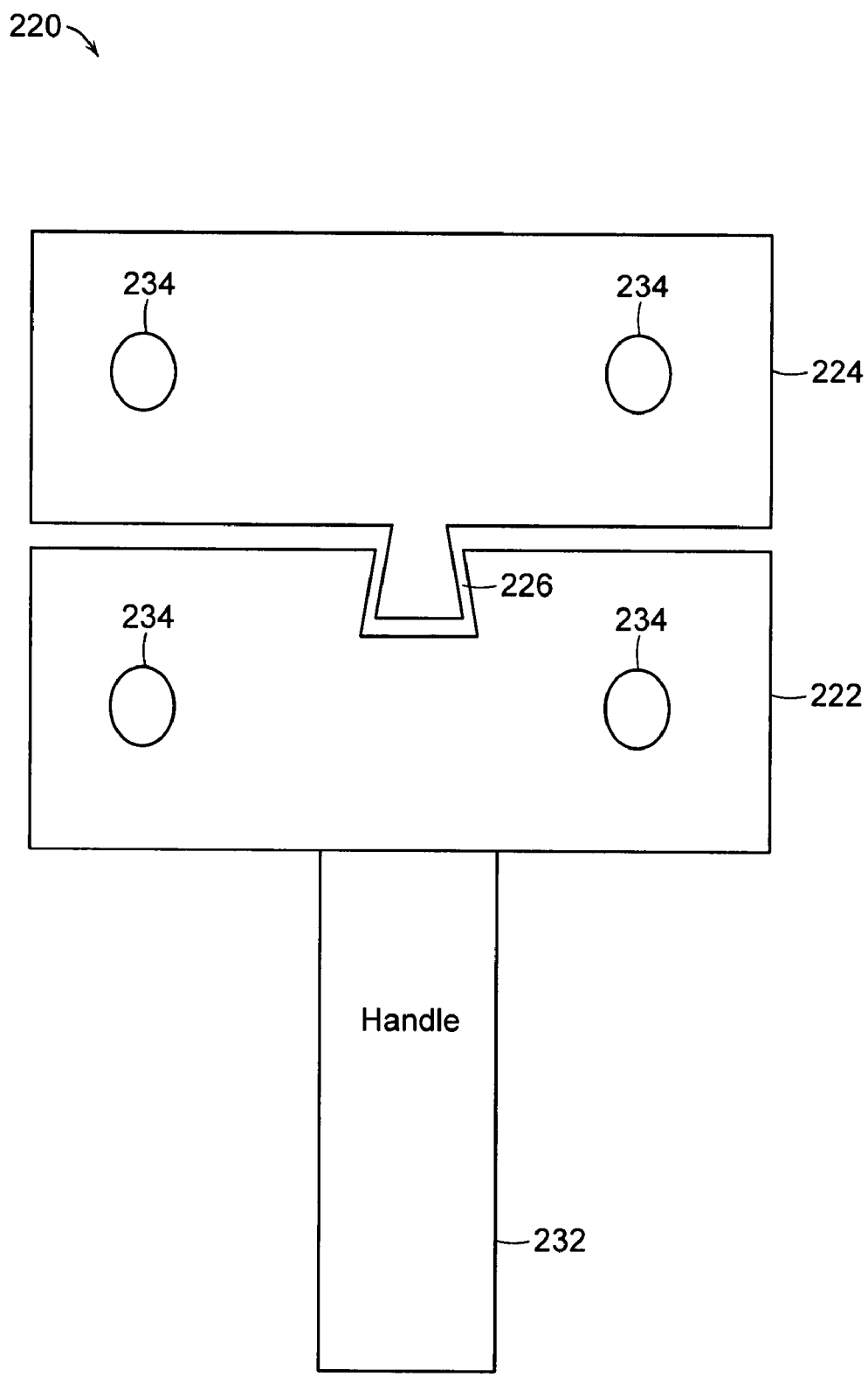
FIG. 26 is a schematic end view of the insertion tool of FIG. 23.
Figure 35:
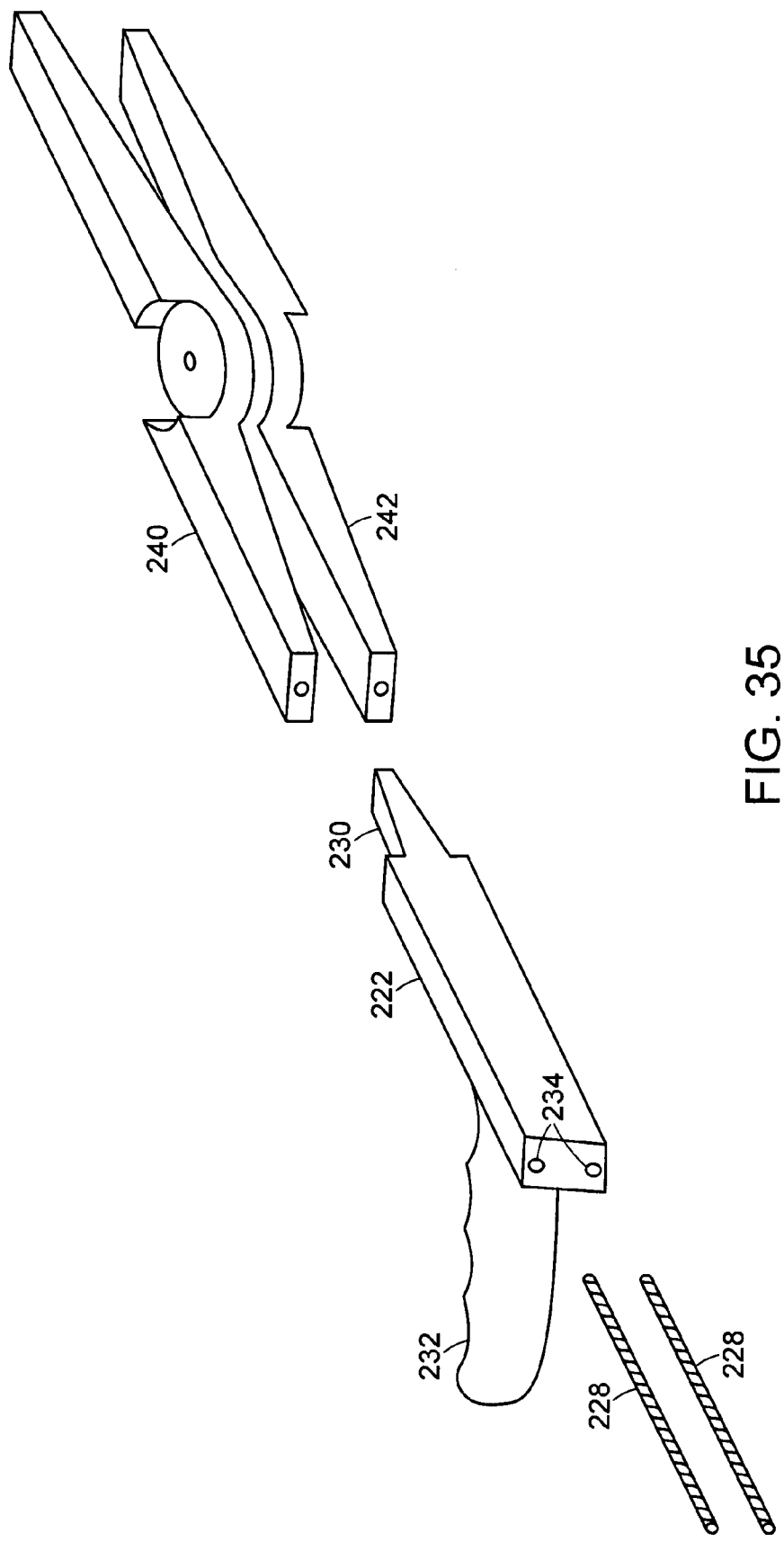
FIG. 35 is a schematic perspective view of the handle side of an insertion tool and two segments of a four segment "scissors" type intervertebral implant, in accordance with one embodiment of the invention.

FIG. 35 shows a schematic perspective view of the main body 222 of an alternative insertion tool 220 with two segments of a four segment "scissors" type intervertebral implant 200. FIG. 25 depicts the wedge shaped end 230 of the main body 222 as it mates with the gap in the implant 200 due to the tapering of the articular surfaces of the upper 202 and lower 204 scissors elements. Also depicted are the alignment paths of the screws 228, through the screw holes 234 in the main body 222 of the insertion tool 220 and into the threaded holes at the distal ends of the elongate elements of the implant 200.

In alternative embodiments of the invention, deployment of the implant 200 can be achieved or aided by a twisting of at least one part of the insertion tool 220 prior to its removal. For example, the wedge shaped end 230 of a main body 222 could be twisted to deploy the upper and lower assemblies prior to removal of the insertion tool 220. This may be advantageous in configurations where the distal ends of the elongated elements of the upper and lower assemblies are to be deployed at different angles on the vertebrae, such that the distal ends of the lower assembly do not lie directly below the distal ends of the upper assembly. A twisting motion of the insertion tool 220 could also be used to trigger a deployment mechanism within the implant 200, such as a spring mechanism.

Figure 36:
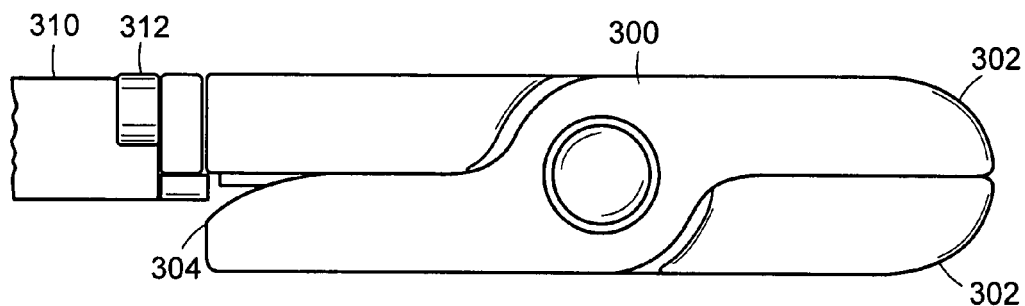
FIG. 36 is a schematic top view of one example of a four segment "scissors" type intervertebral implant, in accordance with one embodiment of the invention.
Figure 37:
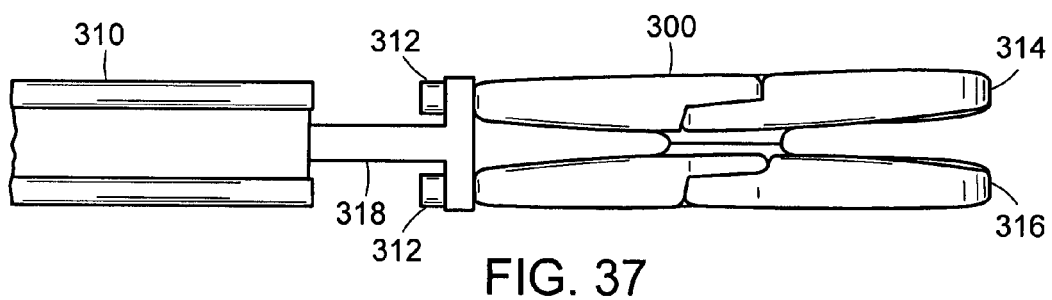
FIG. 37 is a schematic side view of the intervertebral implant of FIG. 36 attached to an alternative insertion tool, in accordance with one embodiment of the invention.

FIGS. 36 and 37 show an alternative embodiment of a four segment "scissors" type intervertebral implant for insertion into an intervertebral space of a spinal column. This implant 300 is similar to that described above with respect to FIGS. 18-22, with an upper scissors assembly 314 and a lower scissors assembly 316, each including two elongate elements pivoting about their central location, and free to articulate about a central mating articulation once released from the insertion tool 310. The implant 300 is releasably connected to the insertion tool 310 by screws 312. The insertion tool works in a manner similar to that described with respect to FIGS. 23-35, but in this case without the need for a dummy support body to be attached to the implant during insertion.

The leading distal edges 302 of the implant 300, i.e., the leading edges of the implant 300 when being inserted into the body, are curved to allow for easier insertion into the body. The shape of the leading edges 302, and the shape of the full cross sectional profile of the implant 300, can be set in certain embodiments to allow for easier insertion into the body to limit soft tissue damage. These changes to the geometry can include further curvature of the leading and side edges, sharp points at the leading edges, or forming the implant with a bullet shaped leading edge.

The trailing edges 304 of two of the elongate elements of the implant 300 are chamfered. This can be advantageous in allowing a distracter wedge to contact and deploy the elongate elements without misalignment. In alternative embodiments, the trailing edges of the implant 300 can be designed to form a number of shapes, including, but not limited to, square, rounded, pointed, or wedge shaped, dependent upon the specific shape of the distracter wedge and the required deployment angle and configuration.

As shown in FIG. 37, the insertion tool 310 includes a T-shaped distal end 318 for attachment with the upper 314 and lower 316 scissors assemblies of the implant 300. In alternative embodiments, this distal end 318 may take other forms, such as, but not limited to, a solid block, a V-shape, a U-shape, or an N-shape.

Figure 38:
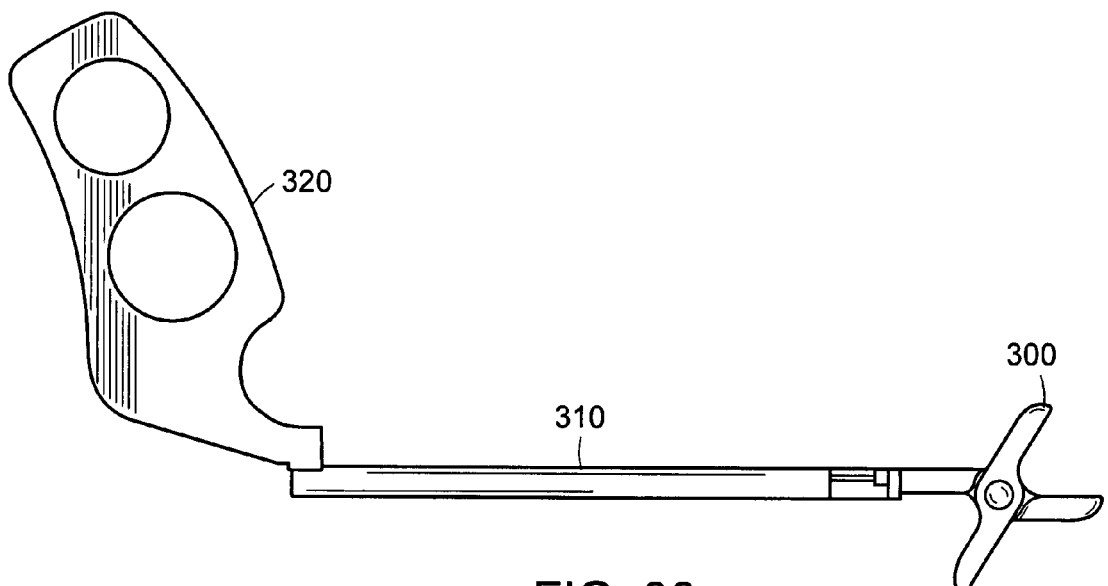
FIG. 38 is a schematic top view of the intervertebral implant of FIG. 36 and insertion tool of FIG. 37.

FIG. 38 shows a top view of the implant 300 attached to the insertion tool 310. The insertion tool 310 is attached to an ergonomic handle 320 to aid a user in guiding and manipulating the insertion tool 310 and implant 300 during insertion. In certain embodiments, the handle 320 can house a trigger or other mechanism that can be connected through the insertion tool to a latch and spring, or other appropriate mechanism, to deploy the implant 300 without the need for a distracter wedge.

FIG. 39 shows the implant 300 and insertion tool 310 being inserted into an insertion housing 330. The insertion housing 330 includes an elongate, hollow body whose dimensions allow the implant 300 and insertion tool 310 to pass therethrough. The housing 330 can have a substantially "C" shaped shell that is enclosed on three sides and at least partially open on a fourth side. The gap in the partially open fourth side can be used as a track to guide the insertion tool 310 and/or implant 300 down the insertion housing 330, and/or to allow bodily matter that may enter the housing 330 during insertion to escape.

The insertion housing 330 also includes a spacer 332 and a wedge shaped leading edge 334 at its distal end. The spacer 332 is a substantially curved or pointed extension at the distal end of the insertion housing 330 that can be used to spread the vertebrae and ease insertion of the implant 300. The wedge shaped leading edge 334 can include a sharp, curved, or pointed edge to ease the insertion of the insertion housing 330 into the body. The spacer 332 can also help in easing the insertion of the housing 330 into the body. The insertion housing 330 can either be inserted into the body prior to the implant 300 and attached insertion tool 310 being inserted into the housing 330, or in an alternative embodiment the implant 300 and attached insertion tool 310 are first inserted into the housing 330 and then the entire apparatus is inserted into the body. As for the previous embodiments, the implant 300 can be inserted through a posterior-lateral, anterior-lateral, or lateral approach. FIG. 40 shows the implant 300 and insertion tool 310 inserted into the insertion housing 330. The housing 330 and insertion tool 310 should be long enough to allow the end of the housing to extend out beyond the skin of a patient, such that the handle 320 of the insertion tool 310 remains outside the body at all times.

Figure 41:
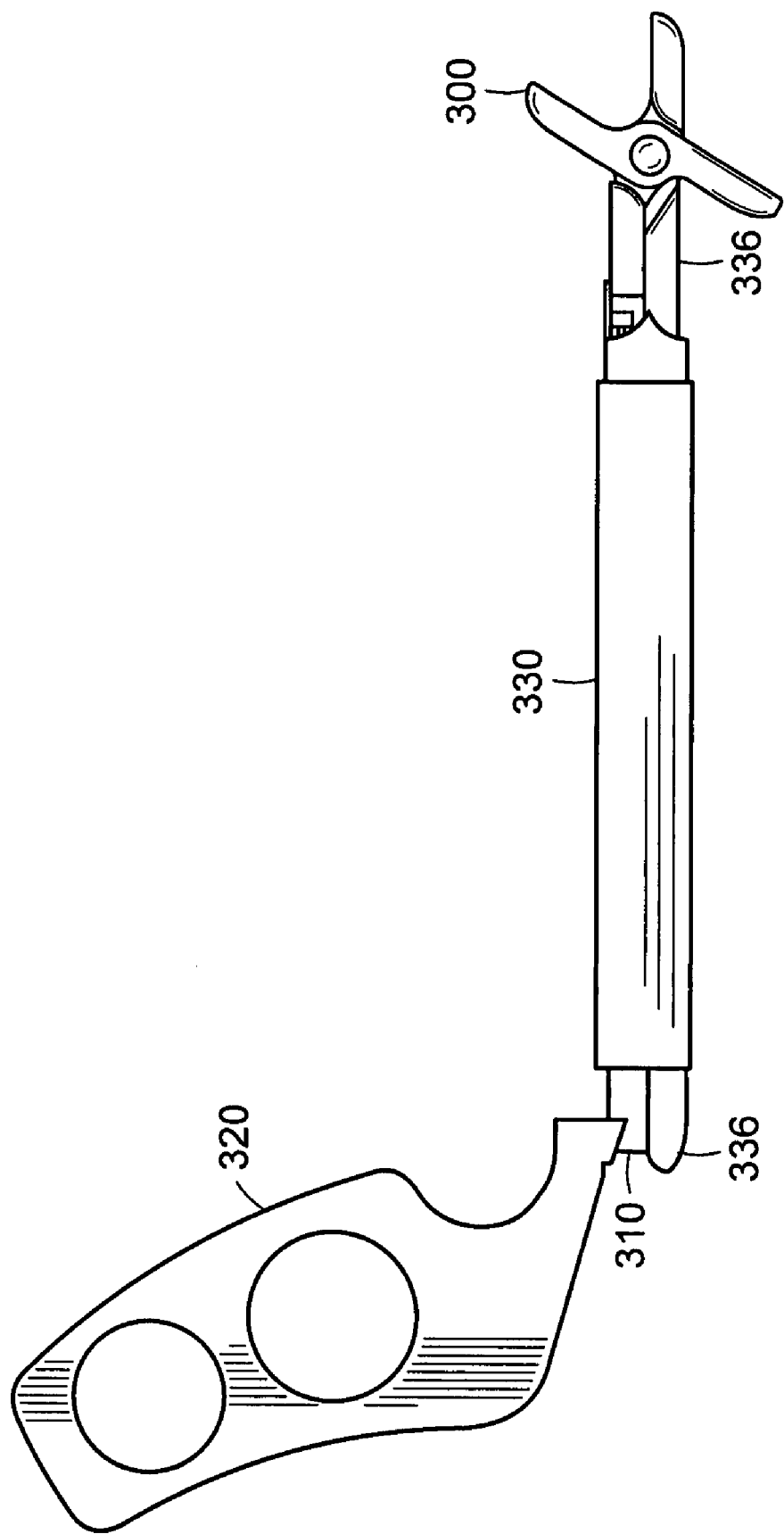
FIG. 41 is a schematic top view of the configuration of FIG. 40 with a distracter wedge deploying the implant.

To deploy the implant 300 into its final extended configuration, a distracter wedge 336 can be passed along the insertion tool 310 and insertion housing 330 to contact the chamfered end 304 of the implant 300. The distracter wedge 336 can then extend the scissors elements out to an angle determined by the size and geometry of the end of the distracter wedge 336, as shown in FIG. 41. The distracter wedge 336 can then be removed, after which the screws 312 can be detached from the implant, using an Allen key or screwdriver, and the insertion tool 310 removed. Finally, the housing 330 can be removed from the body, allowing the vertebrae to settle into place and leaving the deployed implant in position.

Figure 42A:
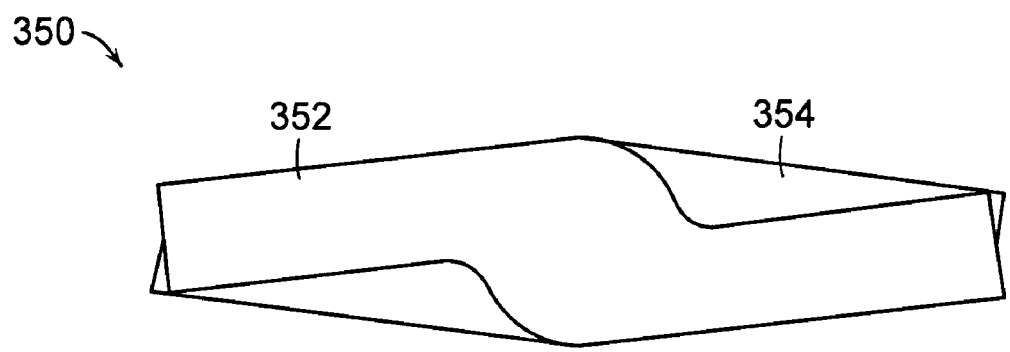
FIG. 42A is a schematic top view of a two segment "scissors" type intervertebral implant configured for minimum cross-sectional profile for insertion, in accordance with one embodiment of the invention.
Figure 42B:
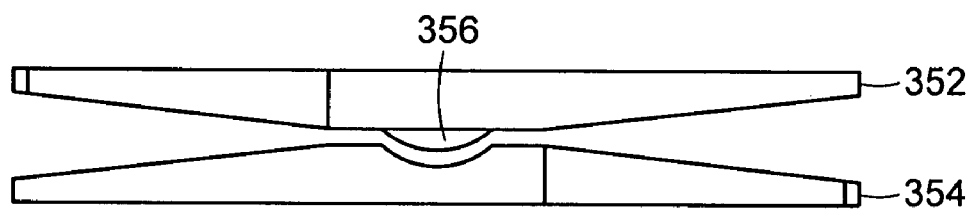
FIG. 42B is a schematic side view of the intervertebral implant of FIG. 42A.

A further embodiment of the invention can be seen in FIGS. 42A and 42B. In this embodiment, an implant 350 includes two elongated elements in a scissors type configuration. The upper elongated element 352 and the lower elongated element 354 can be connected by a mating articulation 356 and/or by a solid or pliable pinned joint. FIG. 42A shows a top view of the implant 350 in an implantation configuration. In this configuration, the elongated elements 352, 354, are turned such that the leading edge of the implant 350 forms the smallest possible profile during insertion. In alternative embodiments of the invention, the leading edges can be curved, pointed, or otherwise shaped to further reduce the cross-sectional profile of the leading edge and thus ease insertion of the implant 350.

In further alternative embodiments, the extended arms of the elongated elements could be hinged, such that the arms fold together during the insertion of the implant 350 and only extend out and lock into a deployed configuration after insertion. These hinged arms could be applied to any of the previously mentioned embodiments to ease insertion of the implant.

Figure 43A:
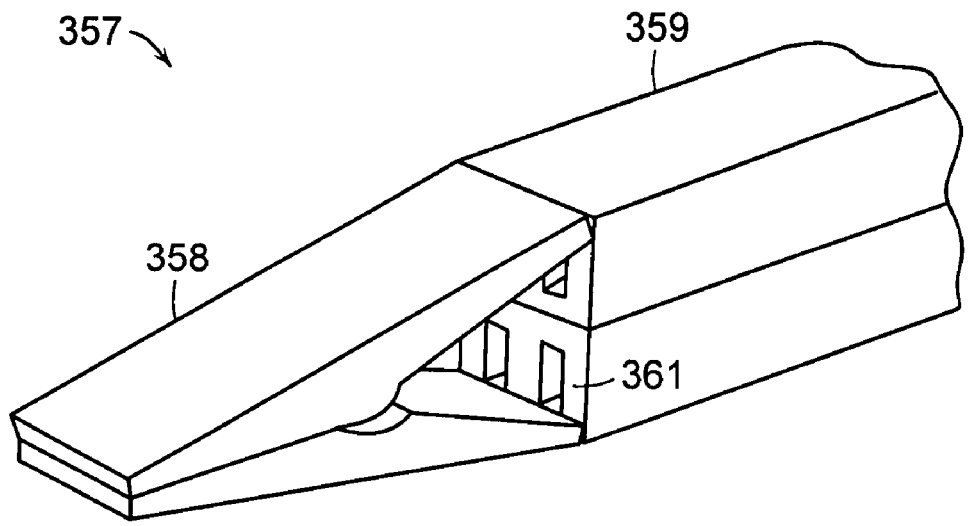
FIG. 43A is a schematic perspective view of a two segment intervertebral implant and slotted insertion tool with a minimum cross-sectional profile at the leading edge during insertion, in accordance with one embodiment of the invention.
Figure 43B:
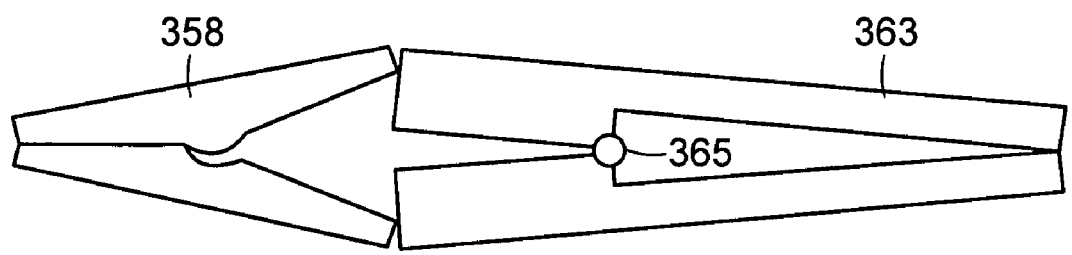
FIG. 43B is a schematic side view of the intervertebral implant of FIG. 43A with a pivotable insertion tool.

Additional embodiments of the invention can be seen in FIGS. 43A and 43B. In this embodiment, a device 357 includes an implant 358 having two parallel elongate elements and an insertion tool 359. The implant 358 can have any design or configuration as described herein, including a scissors type configuration. The insertion tool 359 includes slotted connections 361 that allow the ends of the upper and lower elongate elements of the implant 358 to move up and down with respect to each other. As a result, the implant 358 can be pivoted such that the leading edges of the upper and lower elongate elements of the implant 358 rest against each other, thus forming a substantially wedge shaped profile with a reduced cross-section at the leading edge to ease insertion. By sliding the screws, pins, or other connection elements joining the implant 357 to the insertion tool 359, together with the slotted connections 361, the implant 357 can then be returned to its neutral or parallel configuration prior to being deployed into an open configuration. Alternatively, the implant 357 can return to its parallel configuration while being inserted into the patient, prior to being released by the insertion tool 359. For example, the leading edges of the elongate elements can be manually positioned into the wedge-shaped profile for insertion of the implant and automatically returned to the parallel configuration by the force of the tissue and/or the vertebrae acting on the elongate elements during insertion. In one embodiment, the slotted connections 361 on the insertion tool 359 allow the elongate elements to move relatively freely in the vertical direction, while preventing the implant 358 from deploying into the open configuration.

FIG. 43B shows the implant 358 connected to an alternative insertion tool 363. In this configuration, upper and lower elements of the insertion tool 363 can pivot about an axis 365, such that pinching the ends of the insertion tool 363 together forces the implant 358 into an insertion configuration, with the leading edges of the upper and lower elongate elements of the implant 358 resting against each other, thus forming a substantially wedge shaped profile with a reduced cross-section at the leading edge to ease insertion. Upon or during insertion, the implant 358 can be pivoted into the neutral configuration by pivoting the upper and lower elements of the insertion tool 363 back into a parallel configuration. Alternatively, the insertion tool 363, and by extension the implant, can be biased into the parallel configuration upon removal of the pinching force. Furthermore, the insertion tools 359, 363 can include similar structure and operate similarly as the previously described insertion tools. Additionally, the various features of the implants described with respect to FIGS. 42 and 43 can be combined to reduce both the vertical dimension and the horizontal dimension of the cross-section of the leading edge of the implant.

In alternative embodiments, the insertion tool can include a number of alternative mechanisms to allow the implant to be positioned in both a wedge-shaped insertion configuration and a deployed configuration. These mechanisms can include, but are not limited to, a screw, a wire, a telescope, a spring, a pump, a jack, or another appropriate mechanism. In some embodiments, this mechanism may move the implant 358 manually, while in other embodiments a device could be employed to move the implant 358 automatically upon a triggering input from a user. In certain embodiments, the insertion tool may not need to actively force the implant into the neutral or open configuration, but rather the implant 358 could be moved, for example, from an insertion configuration to a neutral configuration through the force of the upper and lower vertebrae alone, either as the implant 358 is inserted or after the insertion tool is removed.

The above described implants can also take on a number of different shapes other than those described above. For example, the implant can include upper and/or lower assemblies shaped in forms such as, but not limited to, A, H, I, K, M, N, T, W, Y, and Z. These assemblies may be fixed, or may be folded down during insertion and deployed into their final shape after being inserted into the intervertebral space.

Figure 44A:
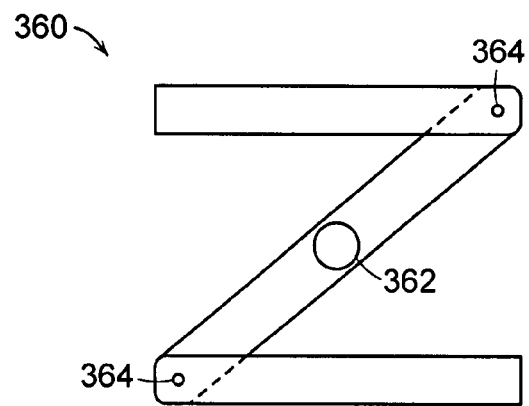
FIGS. 44A-44F are schematic top views of alternative implant assemblies, in accordance with various embodiments of the invention.
Figure 44B:
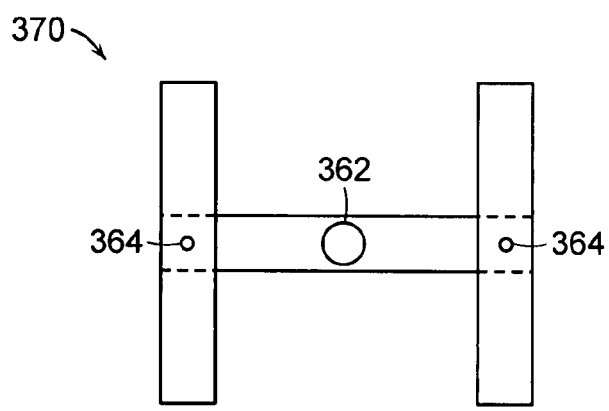
Figure 44C:
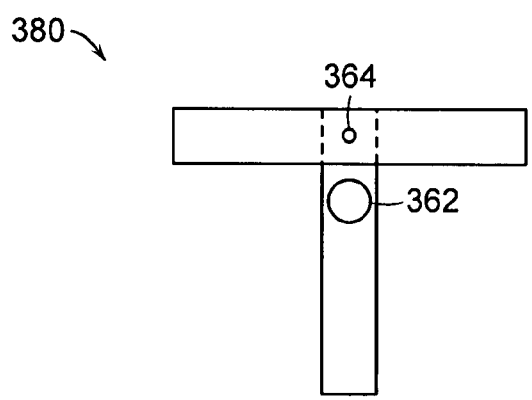
Figure 44D:
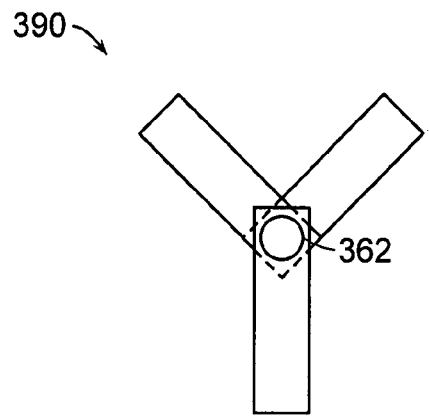
Figure 44E:
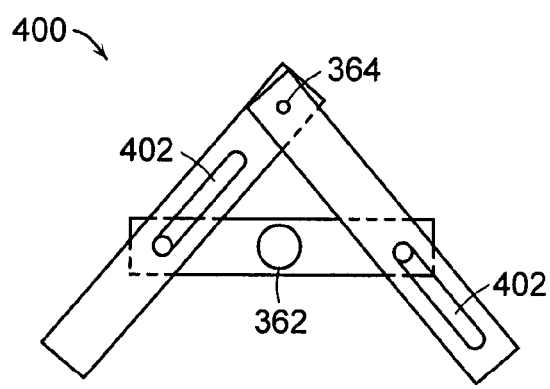
Figure 44F:
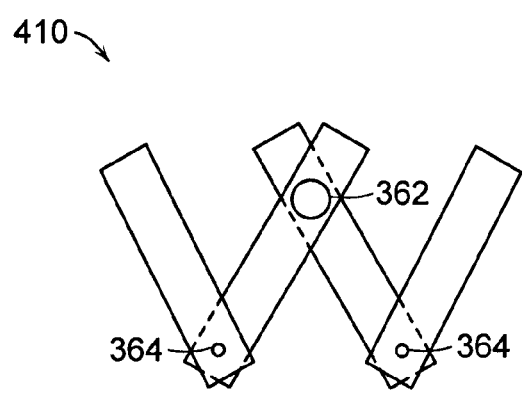

Alternative embodiments of the invention, incorporating a number of different shapes, can be seen in FIGS. 44A-44F. FIG. 44A shows a "Z" shaped assembly 360, FIG. 44B shows an "H" shaped assembly 370, FIG. 44C shows a "T" shaped assembly 380, FIG. 44D shows a "Y" shaped assembly 390, FIG. 44E shows an "A" shaped assembly 400, and FIG. 44F shows a "W" shaped assembly 410.

Each of these embodiments show top views of an implant that includes a mating articulation point 362 at or near the central portion of the assembly. The mating articulation 362 can include any of the methods of mating the upper and lower assemblies of an implant described in the previously mentioned example embodiments. The assemblies also include hinged or pinned connections 364, or other appropriate connection mechanisms, to allow the elongated arms of the implants to fold down to provide a minimal cross-sectional profile during insertion. These arms can then be deployed into a working configuration as described in the previously mentioned embodiments.

In certain embodiments, such as the "A" shaped assembly 400 of FIG. 44E, slots 402, or other appropriate channels or articulating members, can be included to facilitate the folding of the elongated elements down to a minimal cross-sectional profile for insertion.

In further embodiments of the invention, the upper and lower assemblies of the implant can be configured such that they can be inserted into the body in an insertion configuration with a minimal cross-sectional profile, and then be deployed into a working configuration, where the area of the vertebral contacting surface is increased upon deployment. This can expand and/or redistribute the contact points between an implant and a vertebra.

Figure 45A:
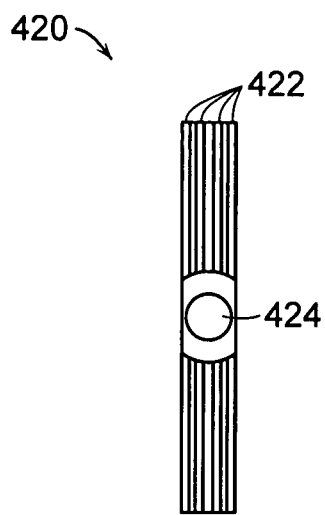
FIGS. 45A and 45B are schematic top views of an alternative implant assembly including an expandable contact surface, in accordance with one embodiment of the invention.
Figure 45B:
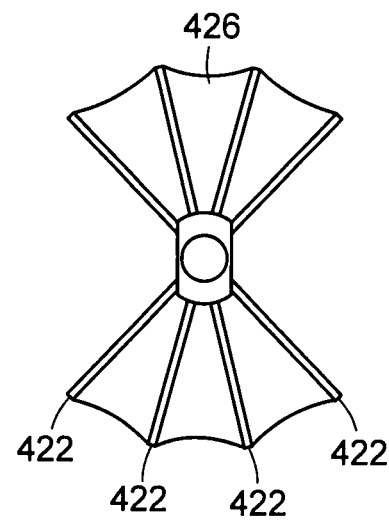

FIGS. 45A and 45B show one embodiment of an implant with the elongated arms extending out from the mating articulation region and including a number of pivotable fingers with a webbing between each finger. In its insertion configuration, as shown in FIG. 45A, the implant 420 includes a number of fingers 424 that are folded together and connect at the mating articulation point 424. Upon deployment of the implant 420, the fingers 422 pivot outwards and extend a webbing material 426 that forms a tight or stiff surface between each finger 422 and thus extends the surface area contacting a vertebra. The webbing 426 can be made from materials such as, but not limited to, an elastic material, a fibrous material, or a stiff corrugated material.

Figure 46A:
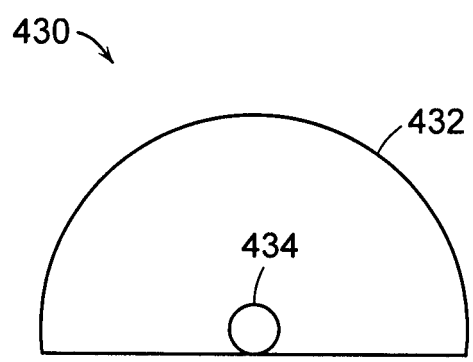
FIGS. 46A and 46B are schematic top views of another alternative implant assembly including an expandable contact surface, in accordance with one embodiment of the invention.
Figure 46B:
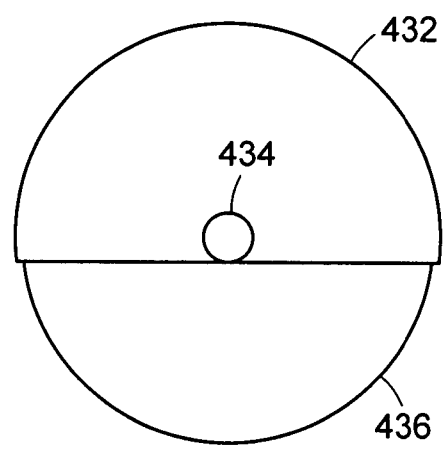

FIGS. 46A and 46B show another embodiment of an implant with a surface area that can be increased upon deployment. In this configuration, an implant 430 includes a first substantially semicircular element 432 with a mating articulation 434 at the radial center of the semicircular element. A second substantially semicircular element 436 is pivotably coupled to the first semicircular element 432, such that it can pivot under the first semicircular element 432 or pivot out and form a substantially circular surface with the first semicircular element 432. In one embodiment, the second semicircular element can be configured to be substantially flush with the first semicircular element upon deployment, such that a substantially planar circular contact surface is formed. FIG. 46A shows the implant 430 in its minimized configuration, for implanting into the intervertebral space. FIG. 46B shows the second substantially semicircular element 436 deployed to maximize the surface area of the implant 430.

The embodiments of FIGS. 45A-B and 46A-B can be advantageous in helping to distribute the load over a maximum area of the vertebrae, thus minimizing the damage to a vertebra through stress caused by the presence of the implant. This increase in surface area upon deployment can also be achieved in other embodiments of the invention, where one surface is positioned under another surface during insertion, such as in certain scissors type embodiments. In an alternative embodiment, a heat dependent polymer, that expands at a certain temperature, can be used to facilitate the increase in surface area of the implant.

In alternative embodiments of the invention, the mating articulation region may be able to be changed when converting from an insertion configuration to a deployed configuration. This change to the mating articulation region may include an increase in the surface area of the mating region and/or a change in the location of the mating articulation in the deployed configuration. These changes in size and/or location of the mating articulation can be advantageous in limiting the profile of the implant during insertion, thus limiting damage to the surrounding tissue during insertion. Increasing the size of the mating articulation region upon deployment can also be advantageous in distributing the load between the upper and lower assemblies of the implant, and can also allow a wider variety of sizes and shapes of mating articulations to be available, depending upon the requirements of the specific implant. Changing the location of the mating articulation for deployment can also be advantageous in allowing the mating articulation to be moved to the center of gravity of a deployed implant after the elongated elements are extended, especially in configurations where the center of gravity of the deployed implant does not conform with the center of any elongated element of the implant. In certain embodiments of the invention, the mating articulation may include one or more distinct, separate elements that can be attached to at least one elongated element of an upper or lower assembly through a connection including, but not limited to, pinned, slotted, threaded, magnetic, or other appropriate connection mechanism. This connection mechanism can enable the mating articulation to change position on the implant from an insertion location to a deployment location.

Figure 47A:
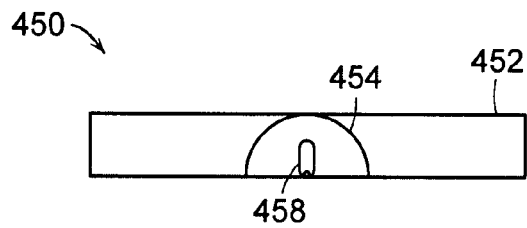
FIGS. 47A-47C are schematic top views of an alternative implant assembly including an expandable and moveable mating articulation, in accordance with one embodiment of the invention.
Figure 47B:
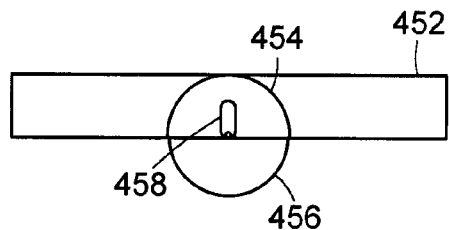
Figure 47C:
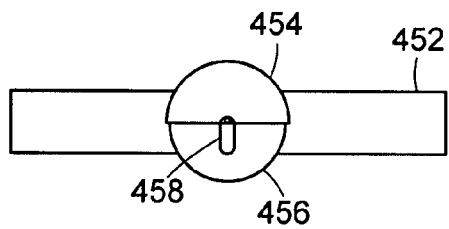

Example embodiments of implants with expandable and/or moveable mating articulations can be seen in FIGS. 47A-C and 48A-B. FIGS. 47A-C show an implant 450 with a mating articulation including a first mating articulation element 454 and a second mating articulation element 456. The mating articulation is connected to an elongated element 452 of the implant 450 through a slotted connection 458. In FIG. 47A, the second mating articulation element 456 is positioned within the first mating articulation element 454 to minimize the cross-sectional profile of the implant 450 for insertion into an intervertebral space. Once inserted into the appropriate position within the intervertebral space, the implant 450 can be deployed. This can include opening the mating articulation by rotating or otherwise moving the second mating articulation element 456 out from the first mating articulation element 454, as shown in FIG. 47B. In certain embodiments, the slotted connection 458 can be used to attach the mating articulation to the elongated element 452, such that after, or possibly before, expanding the mating articulation, the center of the articulation can be moved to a new, deployment location. The positioning of the mating articulation into a final, deployed position can be seen in FIG. 47C. Other means of expanding the articulation surface include those described with respect to FIGS. 45A-B.

Figure 48A:
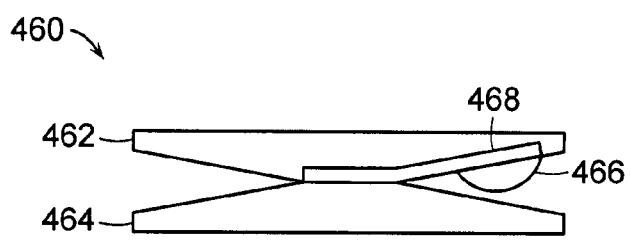
FIGS. 48A and 48B are schematic top views of another alternative implant assembly including a moveable mating articulation, in accordance with one embodiment of the invention.
Figure 48B:
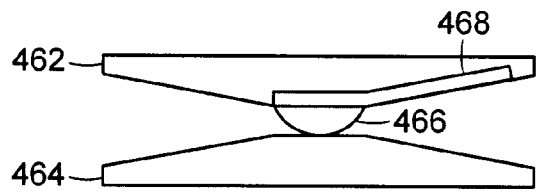

FIGS. 48A-B show an embodiment of an implant 460, where the mating articulation 466 can be moved from one position for insertion of the implant 460 to a second position for deployment of the implant 460. FIG. 48A shows the implant 460 in its insertion configuration, with the cross-sectional profile of the implant 460 minimized to ease insertion into the intervertebral space. The implant 460 includes an upper assembly 462 and a lower assembly 464 that in their deployed configuration contact each other at the location of the mating articulation 466. In the insertion configuration, the mating configuration is moved away from the center of gravity of the implant 460 to lower the profile of the implant 460. This movement can be facilitated by a slotted track 468, or other appropriate means. In alternative embodiments, a pivoting mechanism can be used to move the mating articulation from one configuration to another.

Once inserted into the intervertebral space the implant 460 is set in its deployed configuration. This includes moving the mating articulation 466 along its slotted track 468 to the center of gravity of the implant 460. In certain embodiments of the invention, the center of gravity need not be in the center of a specific elongated element, but may be at or near a distal or lateral edge of an elongated element. The setting of the mating articulation 466 to its deployed configuration can, in certain embodiments, be enabled by the insertion tool or an appropriate surgical tool. In alternative embodiments, springs or other appropriate mechanisms can be included to bias the mating articulation in the deployed position, such that upon deployment, the mating articulation is automatically forced into its deployed position and/or configuration. In other embodiments, the mating articulation can include shape memory materials, such as a heat dependent polymer, that can expand after insertion to either facilitate the increase in size of the mating articulation or help to move the mating articulation from an insertion configuration to a deployment configuration. For example, a material that expands upon heating to body temperature can be placed in the slot 468 of the implant 460 shown in FIGS. 48A-B, to push the mating articulation 466 into its deployment configuration after insertion.

In various embodiments of the invention (see for example FIGS. 18 and 19) the implant can have overall dimensions as follows. The height of the implant, H, can be from about 4 millimeters (mm) to about 20 mm, and preferably from about 7 mm to about 18 mm, and more preferably from about 9 mm to about 16 mm. The width of the implant, W, can be from about 5 mm to about 20 mm, and preferably from about 6 mm to about 16 mm, and more preferably from about 8 mm to about 12 mm. The length of the implant can be from about 15 mm to about 60 mm, and preferably from about 24 mm to about 45 mm, and more preferably from about 28 mm to about 38 mm.

In one embodiment of the invention, the implant can have a height of about 12 mm, a width of about 10 mm, and a length of about 43 mm, or any other dimensions within the recited ranges. These dimensions can be varied dependent upon the location at which the implant is to be placed within an intervertebral space, the size, shape, and physiology of the patient, and the mechanical requirements of the implant to be inserted.

In any of the above embodiments, the intervertebral implant, articulation elements, and/or insertion tool can be made from a material or materials including, but not limited to, stainless steel, aluminum, tantalum, gold, titanium, ceramic, chromium, cobalt, nitinol, metal/ceramic matrices, polytetrafluoroethylene (PTFE), thermoplastic polyurethane (TPU); ethylene vinyl acetate (EVA); thermoplastic polyether block amides; thermoplastic polyester elastomers, nylons, silicones; polyethylenes; polyamides, and polyetheretherketone (PEEK). The implant, articulation elements, and insertion tool may be machined, cast, molded, extruded, or manufactured in any appropriate manner. In certain embodiment each element can be constructed from the same material, but in other embodiments different materials can be used for different elements of the invention, and multiple materials may be used to construct the device.

The invention may be embodied in other specific forms without departing form the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. An intervertebral implant comprising:
 a first assembly comprising at least a first elongate element and a second elongate element contacting the first elongate element;
 a second assembly contacting the first assembly comprising at least a third elongate element and a fourth elongate element contacting the third elongate element; and
 a vertebral contact surface area;
 wherein the first assembly is adapted to articulate relative to the second assembly,
 wherein the first elongate element and second elongate element define a clearance therebetween to enable a limited range of motion between the first elongate element and second elongate element in an interlocked arrangement,
 wherein the first elongate element is on a first plane,
 wherein the second elongate element is on a second plane positioned below the first plane, wherein the third elongate element is on a third plane positioned below the second plane, wherein the fourth elongate element is on a fourth plane positioned below the third plane, and a locking mechanism for preventing relative movement between the first elongate element and second elongate when in a locked configuration and allowing relative movement when in an unlocked configuration.

2. The implant of claim 1, wherein the first elongate element and second elongate element interlock to form an X shape in a plane parallel with the vertebral contact surface area.

3. The implant of claim 1, wherein a first elongate element and second elongate element interlock to form a shape selected from the group consisting of A, H, I, K, M, N, T, V, W, Y, and Z shapes in a plane parallel with the vertebral contact surface area.

4. The implant of claim 1, wherein at least one of the first elongate element and second elongate element comprises a bend.

5. The implant of claim 1, wherein the implant comprises a material selected from the group consisting of stainless steel, aluminum, tantalum, gold, titanium, ceramic, chromium, cobalt, nitinol, metal/ceramic matrices, polytetrafluoroethylene, thermoplastic polyurethane; ethylene vinyl acetate; thermoplastic polyether block amides; thermoplastic polyester elastomers, nylons, silicones; polyethylenes; polyamides, and polyetheretherketone.

6. The implant of claim 1, wherein the third elongate element and fourth elongate element define a clearance therebetween to enable a limited range of motion between the third elongate element and fourth elongate element in an interlocked arrangement.

7. The implant of claim 1, wherein the first elongate element and second elongate element are adapted to be configured in each of a closed position and an open position, wherein the first elongate element and second elongate element are movable relative to one another to be deployable between the closed position and the open position.

8. The implant of claim 7, wherein deployment is effected by a shape memory material.

9. The implant of claim 7, wherein, when the first elongate element and second elongate element are in a closed position, the first elongate element and second elongate element comprise an I shape in a plane parallel with the vertebral contact surface area.

10. The implant of claim 7, wherein, when the first elongate element and second elongate element are in the open position, the first elongate element and second elongate element comprise at least one of an X shape and a Y shape in a plane parallel with the vertebral surface area.

11. The implant of claim 7, wherein the first elongate element and second elongate element are positionable relative to one another through a predetermined angular range between the closed position and the open position.

12. The implant of claim 11, wherein the predetermined angular range comprises a value greater than 0 degrees and less than 180 degrees.

13. The implant of claim 7, wherein the first elongate element and second elongate element assembly are secured by a pivot.

14. The implant of claim 1, wherein the locking mechanism comprises a shape memory material.

15. The implant of claim 1, wherein at least one of the first assembly and the second assembly is adapted for engaging an adjacent vertebral surface.

16. The implant of claim 1 further comprising an articulation region disposed on each of the first assembly and the second assembly.

17. The implant of claim 16, wherein the articulation regions comprise a protuberance disposed on one of the first and second assembly and a mating recess disposed on the other assembly, the protuberance and recess at least partially in contact.

18. The implant of claim 16, wherein the articulation regions are selected from the group consisting of a ball and socket configuration, a male to female configuration, mating arcuate surfaces, and corresponding saddles.

19. The implant of claim 1, wherein at least one of the elongate elements tapers along a length thereof.

20. The implant of claim 1, wherein at least one of the elongate elements defines at least one aperture for enabling in-growth of bone.

21. An intervertebral implant comprising in combination:
a first assembly comprising at least a first elongate element and a second elongate element contacting the first elongate element;
said first elongate element extending non-parallel with said second elongate element;
a second assembly contacting the first assembly comprising at least a third elongate element and a fourth elongate element contacting the third elongate element;
said third elongate element extending non-parallel with said fourth elongate element;
wherein said first assembly is adapted to pivot relative to said second assembly, and
a locking mechanism for preventing relative movement between the first elongate element and second elongate when in a locked configuration and allowing relative movement when in an unlocked configuration.

22. The implant of claim 21 wherein said first elongate element is interlocked together with said second elongate element and said third elongate element is interlocked together with said fourth elongate element.

23. The implant of claim 21 wherein at least one of the first assembly and the second assembly is adapted for engaging an adjacent vertebral surface.

24. The implant of claim 21 wherein an articulation region disposed on each of the first assembly and the second assembly; and
wherein the articulation regions comprise a protuberance disposed on one of the first and second assembly and a mating recess disposed on the other assembly, the protuberance and recess at least partially in contact.

25. The implant of claim 21 wherein an articulation region disposed on each of the first assembly and the second assembly; and
wherein the articulation regions are selected from the group consisting of a ball and socket configuration, a male to female configuration, mating arcuate surfaces, and corresponding saddles.

26. An intervertebral implant comprising:
a first assembly comprising at least a first elongate element and a second elongate element contacting the first elongate element;
a second assembly contacting the first assembly comprising at least a third elongate element and a fourth elongate element contacting the third elongate element; and
a vertebral contact surface area;
wherein the first assembly is adapted to pivot relative to the second assembly,
wherein the first elongate element and second elongate element define a clearance therebetween to enable a limited range of motion between the first elongate element and second elongate element in an interlocked arrangement,
wherein the first elongate element is on a first plane,
wherein the second elongate element is on a second plane positioned below the first plane,
wherein the third elongate element is on a third plane positioned below the second plane,
wherein the fourth elongate element is on a fourth plane positioned below the third plane, and
a locking mechanism for preventing relative movement between the first elongate element and second elongate when in a locked configuration and allowing relative movement when in an unlocked configuration.

* * * * *